United States Patent
Cholette

(10) Patent No.: US 7,634,315 B2
(45) Date of Patent: Dec. 15, 2009

(54) TECHNIQUES TO MONITOR AND TREND NERVE DAMAGE AND RECOVERY

(75) Inventor: Martin Cholette, Acton, CA (US)

(73) Assignee: Pacesetter, Inc., Sylmar, CA (US)

( * ) Notice: Subject to any disclaimer, the term of this patent is extended or adjusted under 35 U.S.C. 154(b) by 413 days.

(21) Appl. No.: 11/756,527

(22) Filed: May 31, 2007

(65) Prior Publication Data

US 2008/0300655 A1  Dec. 4, 2008

(51) Int. Cl.
*A61N 1/05* (2006.01)
*A61N 1/18* (2006.01)

(52) U.S. Cl. .................. 607/2; 607/116; 607/117; 607/118; 600/546; 600/547; 600/548

(58) Field of Classification Search ......... 600/546–548; 607/2, 11, 46–48, 116–118
See application file for complete search history.

(56) References Cited

U.S. PATENT DOCUMENTS

| | | | |
|---|---|---|---|
| 5,540,734 A * | 7/1996 | Zabara | 607/46 |
| 5,702,429 A * | 12/1997 | King | 607/46 |
| 5,860,939 A * | 1/1999 | Wofford et al. | 600/587 |
| 6,070,100 A | 5/2000 | Bakels et al. | |
| 6,238,423 B1 | 5/2001 | Bardy | |
| 6,832,114 B1 | 12/2004 | Whitehurst et al. | |
| 7,192,922 B2 | 3/2007 | Shannon et al. | |
| 7,215,992 B2 | 5/2007 | Stahmann et al. | |
| 7,326,181 B2 * | 2/2008 | Katims | 600/554 |
| 2002/0120200 A1 | 8/2002 | Brockway et al. | |
| 2005/0043675 A1 | 2/2005 | Pastore et al. | |
| 2005/0149151 A1 * | 7/2005 | Orszulak et al. | 607/96 |
| 2005/0288721 A1 | 12/2005 | Girouard et al. | |
| 2006/0116736 A1 | 6/2006 | DiLorenzo | |
| 2006/0178691 A1 | 8/2006 | Binmoeller | |
| 2007/0060971 A1 | 3/2007 | Glasberg et al. | |
| 2009/0062881 A1 | 3/2009 | Gross et al. | |

FOREIGN PATENT DOCUMENTS

| | | | |
|---|---|---|---|
| EP | 1486232 A2 | 12/2004 |
| EP | 1486232 A3 | 12/2004 |
| WO | 2004112563 A2 | 12/2004 |
| WO | 2004112563 A3 | 12/2004 |
| WO | WO2005/087310 | 9/2005 |

OTHER PUBLICATIONS

Bose et al., "Glucagon-Like Peptide 1 Can Directly Protect the Heart Against Ischemia/Reperfusion Injury", Diabetes, vol. 54, Jan. 2005.
Han et al., "Comparisons between neural response imaging thresholds, electrically evoked auditory reflex thresholds and most comfortable loudness levels in CII bionic ear users with HiResolution sound processing strategies", Acta Otolaryngol. Jul. 2005;125(7):732-5.

(Continued)

*Primary Examiner*—Carl H Layno
*Assistant Examiner*—Paula J Stice

(57) ABSTRACT

An exemplary method includes implementing a nerve stimulation therapy that includes delivering stimulation energy to a target nerve, periodically acquiring compound action potentials responsive to the delivered stimulation energy and assessing condition of the target nerve based at least in part on the periodically acquired compound action potentials. Various other exemplary methods, devices, systems, etc., are also disclosed.

14 Claims, 13 Drawing Sheets

OTHER PUBLICATIONS

Kawashima, "The autonomic nervous system of the human heart with special reference to its origin, course, and peripheral distribution", Anat Embryol. (2005) 209: 425-438.

Koga et al., "Selective activation of primary afferent fibers evaluated by sine-wave electrical stimulation", Molecular Pain 20-05, I:13.

Konturek et al., "Brain-gut Axis and Its Role in the Control of Food Intake", J Physiol. Pharma. 2004, 55, 1, 137-154.

Nikolaidis et al., "Recombinant Glucagon-Like Peptide-1 Increases Myocardial Glucose Uptake and Improves Left Ventricular Performance in Conscious Dogs With Pacing-Induced Dilated Cardiomyopathy" Circulation 2004 110: 955-961.

Pauza et al., "Morphology, distribution, and variability of the epicardiac neural ganglionated subplexuses in the human heart", The Anatomical Record (2000) 259(4): 353-38.

Rocca and Brubaker, "Role of the Vagus Nerve in Mediating Proximal Nutrient-Induced Glucagon-Like Peptide-1 Secretion", Endocrinology 140: 1687-1694, 1999.

Schauer et al., "Effect of Laparoscopic Roux-En Y Gastric Bypass on Type 2 Diabetes Mellitus", Ann Surg 2003; 238:467-485.

Taegtmeyer, "Cardiac Metabolism as a Target for the Treatment of Heart Failure", Circulation 2004; 110: 894-896.

Wettergren et al., "The inhibitory effect of glucagon-like peptide-1 (GLP-1) 7-36 amide on gastric acid secretion in humans depends on an intact vagal innervation", Gut 1997;40;597-601.

European Search Report, dated Aug. 1, 2008: Related Application 08251919.0.

European Search Report, dated Aug. 1, 2008: Related Application 08251920.0.

NonFinal Office Action, mailed Sep. 4, 2009 - Related U.S. Appl. No. 11/756,435.

NonFinal Office Action, mailed Sep. 4, 2009 - Related U.S. Appl. No. 11/756,451.

NonFinal Office Action, mailed Sep. 10, 2009 - Related U.S. Appl. No. 11/756,464.

NonFinal Office Action, mailed Sep. 10, 2009 - Related U.S. Appl. No. 11/756,478.

NonFinal Office Action, mailed Sep. 9, 2009 - Related U.S. Appl. No. 11/756,515.

NonFinal Office Action, mailed Jul. 23, 2009 - Related U.S. Appl. No. 11/756,405.

* cited by examiner

Nervous System and
Nervous System Effectors

TECHNIQUES TO MONITOR AND TREND NERVE DAMAGE AND RECOVERY

RELATED APPLICATIONS

This application is related to the following co-pending U.S. patent application Ser. Nos.:

Ser. No. 11/756,405, filed May 31, 2007, entitled "Energy Delivery to the Gastric System for Treating Metabolic Disorders;"

Ser. No. 11/456,435, filed May 31, 2007, entitled "Energy Delivery to the Gastric System for Treating Metabolic Disorders;"

Ser. No. 11/756,451, filed May 31, 2007, entitled "Treatment of Cardiomyopathy, Heart Failure and Cardiac Ischemia using Stimulation Induced Secretion of GLP-1;"

Ser. No. 11/756,464, filed May 31, 2007, entitled "Treatment of Cardiomyopathy, Heart Failure and Cardiac Ischemia using Stimulation Induced Secretion of GLP-1;"

Ser. No. 11/756,478, filed May 31, 2007, entitled "Treatment of Cardiomyopathy, Heart Failure and Cardiac Ischemia using Stimulation Induced Secretion of GLP-1;" and Ser. No. 11/756,515, filed May 31, 2007, entitled "Treatment of Cardiomyopathy, Heart Failure and Cardiac Ischemia using Stimulation Induced Secretion of GLP-1."

TECHNICAL FIELD

Exemplary methods, devices, systems, etc., presented herein generally relate to using an implantable device to acquire compound action potentials for use in diagnosis of nerve condition.

BACKGROUND

Various therapies rely on nerve stimulation using an implantable neurostimulation device. Such therapies require implantation of an electrode or other actuator (electromagnetic, chemical, mechanical, heat, etc.) to activate a nerve where such activation forms part of a therapy. Activation may include blocking nerve transmission or otherwise altering a nerve in a manner that provides for or augments a therapy.

The aforementioned types of therapies rely at least to some degree on nerve condition. Nerve condition can be compromised at time of implant, by delivery of a therapy, by medication, by patient health, etc. Various exemplary techniques described herein provide for acquisition of compound action potentials and analysis of such potentials, for example, to allow a clinician to assess nerve condition, particularly over time.

SUMMARY

An exemplary method includes implementing a nerve stimulation therapy that includes delivering stimulation energy to a target nerve, periodically acquiring compound action potentials responsive to the delivered stimulation energy and assessing condition of the target nerve based at least in part on the periodically acquired compound action potentials. Various other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

Divisions of the human nervous system include cranial nerves, central nerves, peripheral nerves and autonomic nerves. In general, cranial nerves convey information between the brain and the sensory organs of the head (e.g., eyes, ears, mouth, etc.); central nerves convey information between the spinal cord and the brain; peripheral nerves convey information between the spinal cord and peripheral parts of the body (e.g., arms, hands, legs, feet); and autonomic nerves convey information between the spinal cord and brain and organs such as the heart, lungs, stomach, intestines, bladder, sex organs, etc. The human nervous system also includes some localized systems. For example, some nerves convey information from one part of an organ to another part of an organ (e.g., consider intestinal nerves that convey information from a proximal site to a distal site).

Figure 1:
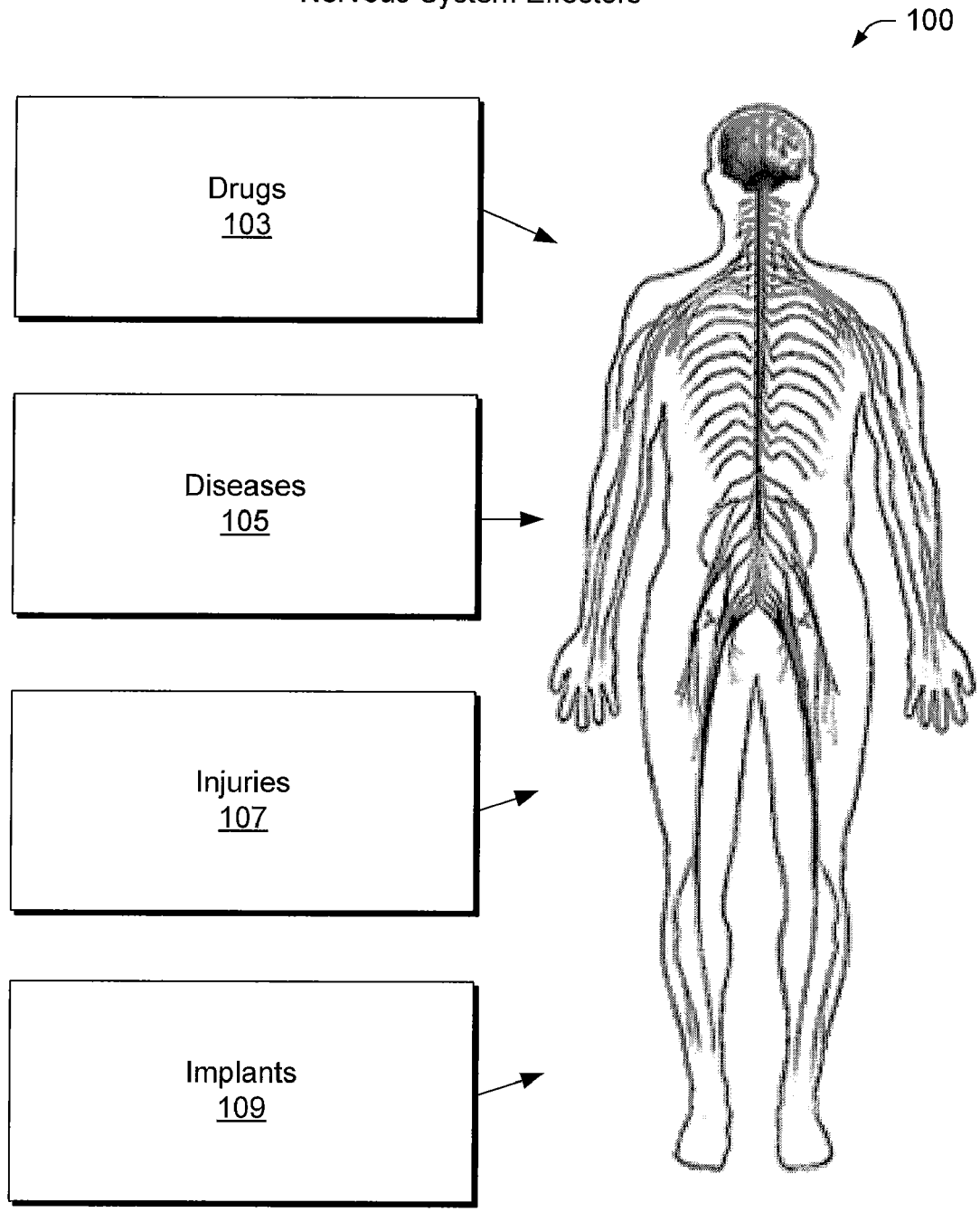
FIG. 1 is a diagram of the nervous system of the body and various effectors that can affect nerve condition.

FIG. 1 shows an approximate anatomical diagram of the nervous system 100 along with various effectors 103, 105, 107, 109 that can affect the nervous system 100 positively or negatively. An effector may be a substance, procedure, condition, device or agent that produces an effect on the nervous system 100. For example, drugs 103, diseases 105, injuries 107 and implants 109 can affect the nervous system 100.

With respect to drugs 103, long-term medication can impair the nervous system as can drug abuse (e.g., inhalants such as nitrites, solvents, aerosols, etc.). On the other hand, some drugs can protect or promote regeneration of the nervous system. For example, cytoprotectants are compounds that reduce free radicals (e.g., free radical trapping agents) and may protect tissues against the damage caused by free radicals that occurs during stroke and other ischemic conditions. Cytoprotectants may prove useful for the treatment of myocardial infarction, kidney disease, stroke, neurodegeneration and potentially other diseases and conditions.

With respect to diseases 105, diabetes, multiple sclerosis, amyotrophic lateral sclerosis, etc., can cause nerve degeneration. A general term for degeneration of the nervous system is neuropathy. Peripheral neuropathy, also known as peripheral nerve disease, afflicts about 15 to 20 million in the United States. It is caused by deterioration of the peripheral nerves and disrupts the body's ability to communicate with its muscles, organs and tissues. Symptoms include unusual or unpleasant irritations including tingling, burning, itchiness, crawling sensation, dizziness, clumsiness, etc.

As neuropathy is a broad term, it has many causes including: alcoholism, amyloidosis (metabolic disorder), autoimmune disorders (e.g., Guillain-Barr syndrome), Bell's palsy, cancer, Charcot-Marie-Tooth disease, carpal tunnel syndrome, chronic kidney failure, connective tissue disease (e.g., rheumatoid arthritis, lupus, sarcoidosis), diabetes mellitus, infectious disease (e.g., Lyme disease, HIV/AIDS, hepatitis B, leprosy), liver failure, medications (see drugs 103 above), radiculopathy, vitamin deficiencies (e.g., pernicious anemia).

More specifically, types of neuropathies include chronic autoimmune neuropathies (a diverse group of syndromes that result from immune-mediated damage to the peripheral nerves), diabetic neuropathies (most common cause of neuropathy in the Western world, which may occur in both type I and type II diabetes), nutritional neuropathies (malnutrition, alcoholism, reduced absorptive surface as a result of gastric bypass or other procedure, intestinal wall infiltration due to Crohn's disease, etc.), tumor related neuropathies, infectious disease related neuropathies, hereditary disease related neuropathies, etc.

With respect to injuries 107, many types of trauma can cause nerve problems, including acute trauma and trauma due to long term compression or repetitive motion, etc. Surgery causes trauma and may be considered a form of injury.

With respect to implants 109, an implant typically requires some degree of invasive or surgical procedure. Further, where an implant is associated with a nerve, various types of interactions may occur between the implant and the nerve whether at the time of implant and/or after implant. In addition, the body's immune system may respond to an implant as a foreign body. A concept germane to this latter issue is biocompatibility. Biocompatibility may be defined on the basis of material used or the nature of an implant.

Various neurostimulation devices electrically stimulate peripheral nerves (e.g., vagus for the treatment of obesity, phrenic for the treatment of sleep apnea, pudendal for urinary incontinence) with the use of a lead that includes one or more electrodes. Such a lead may include a wrap, a cuff, a helix, etc., that positions an electrode or electrodes on a nerve. Thus, some interaction occurs between the implant and a nerve, which may cause some degree of injury (e.g., typically minor and reversible) to the nerve. In some cases, the damage can be immediate such as iatrogenic trauma during surgery. In some cases, the damage can be due to chronic mechanical stress (or immune stress) and can take weeks or months to manifest or stabilize. Of concern for delivery of therapy is the risk that the magnitude of the damage is at a level that interferes with delivery of therapy or the effect of the therapy. In a worst case scenario, nerve injury may be of a level that completely blunts the effect of the therapy for some extended amount of time.

Various exemplary methods, devices, systems, etc., described herein include measuring nerve action potential information and analyzing such information for indicia of nerve damage. Various techniques include presenting information in graphical form to thereby allow a clinician to monitor or assess nerve condition. Various techniques include quantifying damage as well as recovery of a damaged nerve. Such exemplary techniques may be used for programming and fine tuning a neurostimulation device that delivers any of a variety of therapies (e.g., obesity, apnea, autonomic, incontinence, epilepsy, depression, etc.).

A single implantable medical device may be manufactured from many materials that may form part of an exposed surface. In general, pre-clinical testing of such materials occurs prior to implant of a device. Further, shape and geometry of a device may also be considered for affect on a device's biocompatibility.

Using a scheme that considers nature of a device, definitions for biocompatibility of long-term implanted devices, short-term implanted devices and tissue-engineered products may be considered. The biocompatibility of a long-term implantable medical device refers to the ability of the device to perform its intended function, with the desired degree of incorporation in the host, without eliciting any undesirable local or systemic effects in that host. With respect to a short-term implantable device, biocompatibility of a medical device that is intentionally placed within the cardiovascular system for transient diagnostic or therapeutic purposes refers to the ability of the device to carry out its intended function within flowing blood, with minimal interaction between device and blood that adversely affects device performance, and without inducing uncontrolled activation of cellular or plasma protein cascades. Biocompatibility of tissue-engineering products considers biocompatibility of a scaffold or matrix for a tissue-engineering products and to its ability to perform as a substrate that will support the appropriate cellular activity, including the facilitation of molecular and mechanical signaling systems, in order to optimize tissue regeneration, without eliciting any undesirable effects in those cells, or inducing any undesirable local or systemic responses in the eventual host.

As described herein, various exemplary methods, devices, systems, etc., can assess nerve condition. Such assessment may be beneficial in establishing a relationship between nerve condition and a drug 103, nerve condition and a disease 105, nerve condition and an injury 107 and/or nerve condition and an implant 109.

Figure 2:
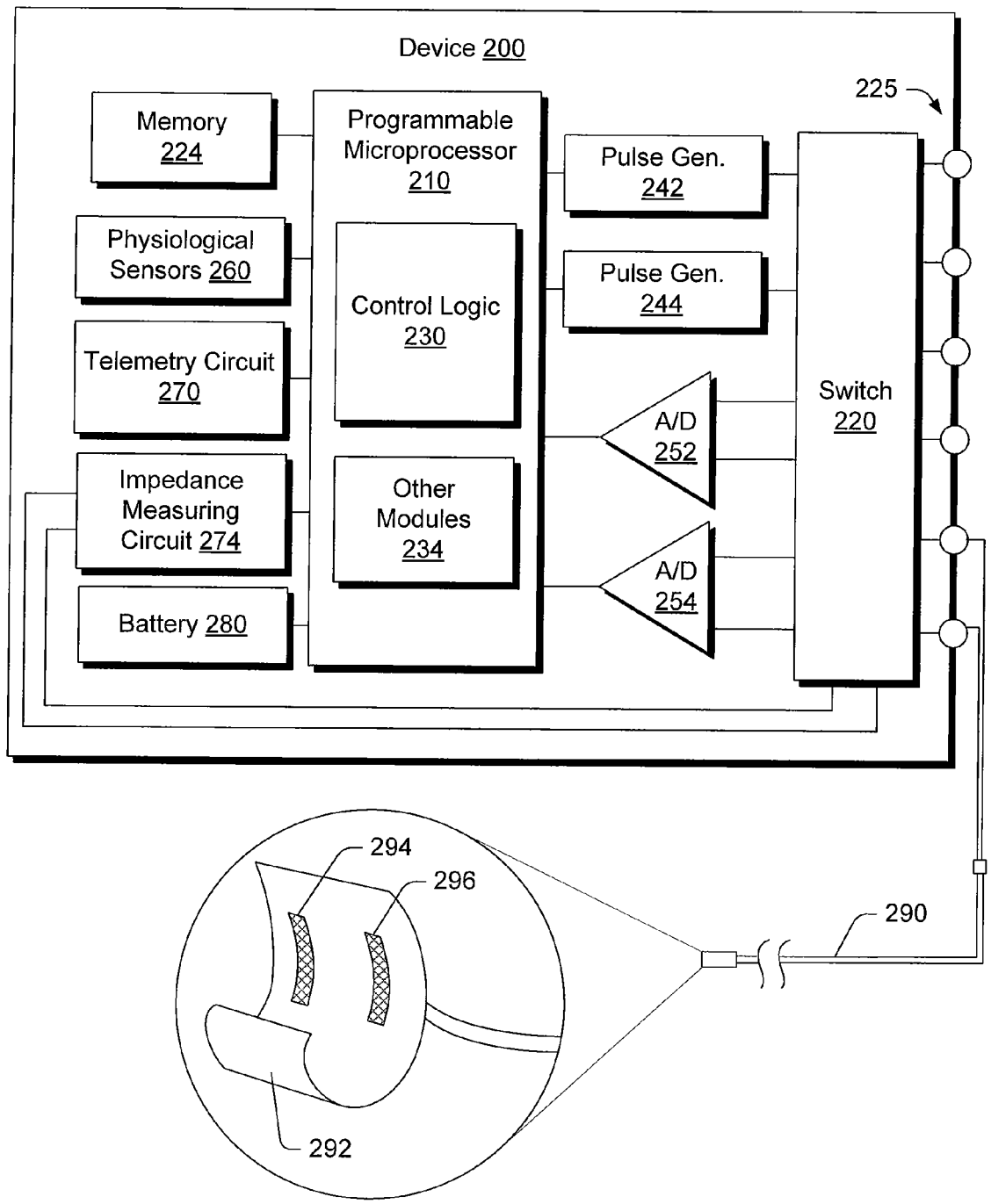
FIG. 2 is a functional block diagram of an exemplary implantable device illustrating basic elements that are configured to allow for acquisition of compound action potentials.

FIG. 2 shows a block diagram of an exemplary device 200 capable of sensing, activating and/or blocking activity of any number of organs, muscles and/or nerves. A basic device may include a processor, memory, one or more inputs, one or more outputs and control logic stored as instructions in the memory and operable in conjunction with the processor. The device 200 includes various additional features.

The exemplary device 200 includes a programmable microprocessor 210 that can implement control logic 230 and other instructional modules 234. Information may be stored in memory 224 and accessed by the programmable microprocessor 210. For delivery of activation energy, the device 200 includes one or more pulse generators 242, 244. The pulse generators 242, 244 may rely on a switch 220 for delivery of energy via one or more connectors 225. While a device may include one or more integral leads, in general, a device includes one or more connectors for connecting a lead or leads to the device. More particularly, the connectors 225 provide for electrically connecting one or more electrodes to the circuitry of the device 200. In the example of FIG. 2, the switch 220 may select an appropriate electrode configuration. An electrode configuration may include an electrode from one lead and an electrode from another lead, a case electrode and another electrode or electrodes from a single lead.

The device 200 further includes one or more analog to digital converters 252, 254 for converting analog signals to digital signals or values. The processor 210 may use a signal provided by one of the A/D converters 252, 254 to control a therapy or other process. A control signal from the processor 210 may instruct the switch 220 to select a particular electrode configuration for sensing electrical or other activity. As discussed below, various techniques include sensing nerve activity or other activity.

The device may include one or more physiological sensors 260. Such sensors may be housed within a case of the device 200 (e.g., a motion sensor), include a surface mounted component, include a lead, include a remote sensor, etc. A sensor may provide a digital signal or an analog signal for use by the processor 210 or other circuitry of the device 200. A physiological sensor may provide a signal via one or more of the connectors 225.

For purposes of communication with external or other implantable devices, the device 200 includes a telemetry circuit 270. The telemetry circuit 270 may include one or more antennae for transmission and/or receipt of electromagnetic signals. Such a circuit may operate according to a specialized frequency or frequencies designated for medical devices. Various conventional implantable devices rely on an associated programmer, which is an typically an external computing device with a communication circuit suitable for communicating with an implantable device for purposes of data transfer, status checks, software download, etc. Where the circuit 270 communicates with an implantable device or a device in electrical connection with a patient's body, then the body may be a conductive medium for transfer of information. For example, the circuit 270 may be capable of communication with a specialized wristwatch where the body is relied upon as a conductor.

The device 200 further includes an impedance measuring circuit 274. Such a circuit may rely on instructions from the processor 210. For example, the processor 210 may instruct the circuit 274 to provide a measured impedance for a particular electrode configuration. In such an example, the processor 210 may also instruct the switch 220 to provide the circuit 274 with a particular electrode configuration. Impedance information may be used by the processor 210 for any of a variety of purposes. The processor 210 may store impedance or other information to memory 224 for later use or for transmission via the telemetry circuit 270.

The device 200 includes a power source, which is shown as a batter 280 in the example of FIG. 2. The battery 280 powers the processor 210 and optionally other circuitry, as appropriate. In general, the battery 280 provides power to the pulse generators 242, 244. Consequently, the battery 280 provides for operation of circuitry for processing control logic, etc., and provides for energy to activate tissue. A lead-based sensor may connect to the device 200 via one or more of the connectors 225 and be powered by the battery 280. The battery 280 may be rechargeable, replaceable, etc.

While the device 200 includes particular features, various exemplary devices, systems, methods, etc., may use or be implemented using a different device with more or less features.

FIG. 2 also shows an exemplary lead 290 connected to the device 200 via one or more of the connectors 225, which can provide for electrical connections to one or more electrodes. In the example of FIG. 2, the lead 290 includes an attachment mechanism 292 to position two electrodes 294, 296 on a nerve to acquire nerve activity and/or to delivery activation energy to a nerve. While a wrap 292 that can wrap around a nerve is shown in FIG. 2, an attachment mechanism may be a cuff, a spiral, a stitch, etc. Further, one or more attachment mechanisms may be used. Thus, as described herein, an exemplary device optionally includes, or connects to, one or more electrodes for sensing nerve activity and/or stimulating a nerve.

Table 1 lists various types of nerve fibers. Sensory neurons can be divided into generally into four types: A$\alpha$ fiber, A$\beta$ fiber, A$\delta$ fiber, and C fiber neurons. The A$\alpha$ and A$\beta$ fiber neurons mediate normal sensation (for example, proprioception and light touch), whereas A$\delta$ and C fiber neurons primarily mediate noxious stimuli and are defined as nociceptive neurons. Based on electrophysiological characteristics, the A-delta fiber neurons are subdivided into two types.

More generally, an A fiber may be defined as any of the myelinated nerve fibers in somatic nerves, measuring 1 to 22 microns in diameter, conducting nerve impulses at a rate of 6 to 120 meters per second; a B fiber may be defined as any of the myelinated nerve fibers in autonomic nerves, having a diameter of 2 microns or less, conducting nerve impulses at a rate of 3 to 15 meters per second; and a C fiber as any of the unmyelinated fibers, 0.4 to 1.2 micrometers in diameter, conducting nerve impulses at a velocity of 0.7 to 2.3 meters per second.

TABLE 1

Types of Nerve Fibers

| Fiber Types | Fiber Diameter (μm) | Cond. Velocity (m/s) | AP Duration (ms) | Absolute Refractory (ms) | Functions |
|---|---|---|---|---|---|
| Aα motoneurones | 12-22 | 70-100 | 0.4-0.5 | 0.2-1.0 | Efferent alpha Afferent muscle spindles, tendon organs |
| Aβ | 5-13 | 15-70 | 0.4-0.5 | 0.2-1.0 | Afferent, cutaneous, Touch, pressure |
| Aγ | 3-8 | 15-40 | 0.4-0.7 | 0.2-1.0 | Gamma motoneurons |
| Aδ | 1-5 | 5-30 | 0.2-1.0 | 0.2-1.0 | Afferent, fast Pain, temperature |
| B | 1-3 | 3-15 | 1.2 | 1.2 | Efferent, autonomic Only preganglionic |
| C | 0.2-1.2 | 0.2-2.0 | 2 | 2 | Afferent, "slow" Pain, Efferent Autonomic postganglionic |

Figure 3:
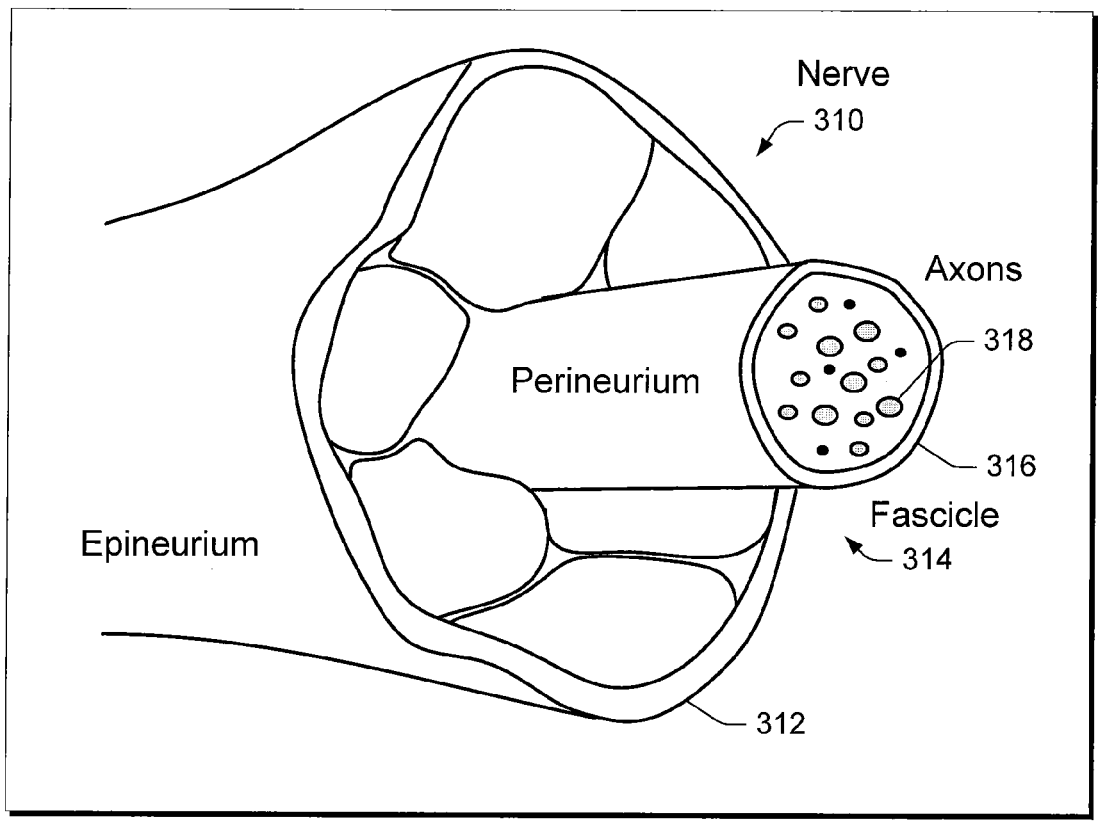
FIG. 3 is a diagram of a nerve and a plot of various compound action potentials.
Figure 3:
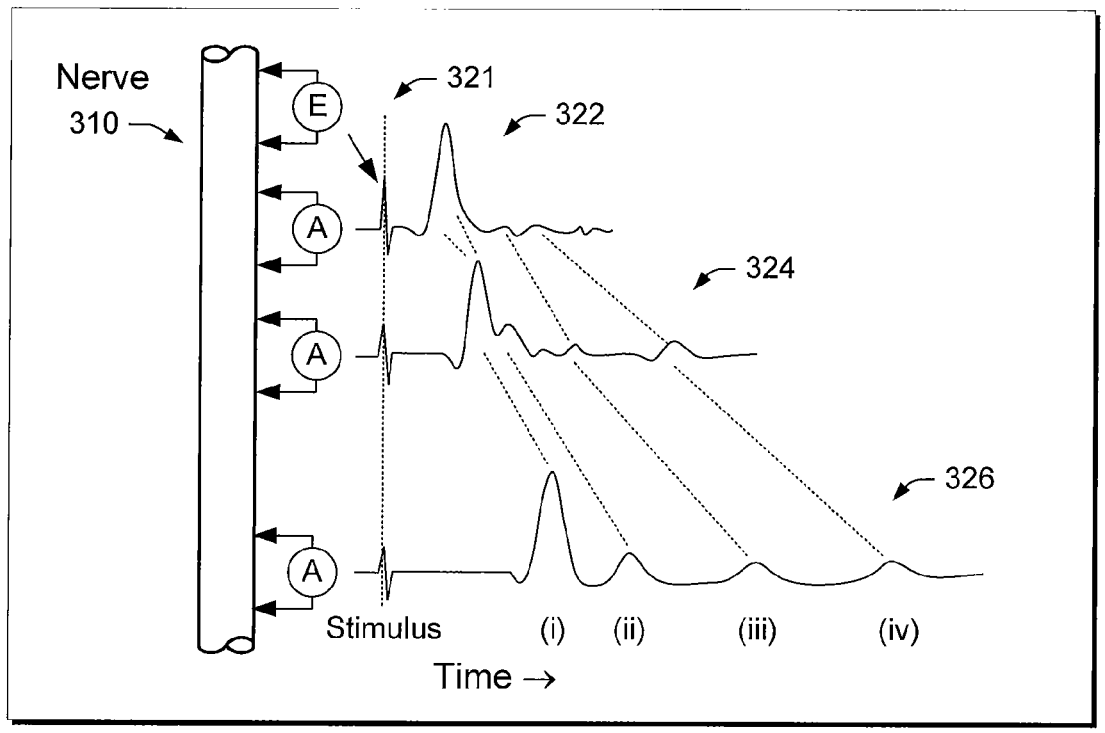

FIG. 3 shows a nerve 310 and various features to the level of individual axons 316. The nerve 310 has an outer layer known as the epineurium 312 that surrounds some fascicles 314. The epineurium 312 acts as a connective tissue framework and sheath to bind together nerve bundles, known as fascicles 314. Each fascicle 314 has an outer connective tissue sheath known as the perineurium 316 and each fascicle 314 includes individual axons 318, which may be of more than one nerve type. Depending on size, a fascicle may be referred to as a funiculus and a fascicle may be considered as including more than one funiculi.

Not shown in FIG. 3 is the neurolemma (or neurilemma or sheath of Schwann), which is the outermost layer of nerve fibers in the peripheral nervous system. The neurolemma is a nucleated cytoplasmic layer of Schwann cells that surrounds the myelin sheath of axons. Unlike the axon and the myelin sheath, the neurolemma does not degenerate after a nerve has been cut or crushed; the hollow tube formed by the neurolemma is instrumental in regenerating the nerve fiber.

With respect to Schwann cells, these are a variety of neuroglia that mainly provide myelin insulation to axons in the peripheral nervous system. The nervous system relies on this myelin sheath for insulation and as a method of decreasing membrane capacitance in the axon, thus allowing for saltatory conduction to occur and for an increase in impulse speed, without an increase in axonal diameter. Non-myelinating Schwann cells are involved in maintenance of axons and are crucial for neuronal survival. Some group around smaller axons and form Remak bundles. Schwann cells may be viewed as the peripheral nervous system's analogues of the central nervous system oligodendrocytes.

Each Schwann cell can cover about a millimeter along an axon and hence hundreds and often thousands are needed to completely cover an axon. Gaps between Schwann cell covered segments are known as Nodes of Ranvier, important sites of ionic and other exchanges of the axon with the extracellular liquid. Unlike oligodendrocytes, myelinating Schwann cells provide insulation to only one axon. This arrangement permits saltatory conduction of action potentials which greatly speeds it and saves energy.

Referring again to FIG. 2 and, in particular, the lead 290, in general, it is easier to implant electrodes around a nerve as opposed to within a nerve. As a result, the electrode arrangement of the lead 290 is suited to acquire electrical information from a nerve or nerve bundle, as opposed to electrical information for a single axon or nerve fiber (see, e.g., fiber diameters of Table 1).

The signal acquired from a nerve or nerve bundle is referred to as a compound action potential and used as an indicator of neural transmission. A compound action potential (CAP) is a signal recorded from a nerve trunk made up of numerous axons. It is the result of summation of many action potentials from the individual axons in the nerve trunk.

As shown in FIG. 3, a CAP 322 may be initiated on a peripheral nerve by an electrical stimulus 321 applied to the nerve at some point at a distance from the recording site. FIG. 3 shows three acquisition sites "A" at particular distances from a stimulation site "E" where energy is delivered to a nerve 310. As indicated by the electrograms 322, 324, 326, latency between the application of the stimulus and the onset of a CAP is, in part, a function of the distance between the acquisition site and the site where energy is delivered (whether electrical, chemical, mechanical, thermal, etc.). In FIG. 3, an initial biphasic spike is a signal artifact associated with delivery of energy (E). As the distance between the acquisition site (A) and the delivery site (E) increases, various features of the CAP change. For example, the different conduction velocities of an axon population may result in a shift in time of the amplitude peaks as the distance increases away from the energy delivery site.

For a nerve that contains A, B, and C type fibers, the responses from these different fiber types are distributed along the time axis because each of these fiber types has a different conduction velocity (see Table 1). As a result, action potentials from fibers with a slower conduction velocity take longer to travel from the activation site to a sensing or acquisition site, which can be used to calculate the conduction velocity of the various types of axons within a nerve. Conduction velocity information can be used to classify the nerve types contributing to a CAP.

While a nerve may include different types of fibers where conduction velocities may differ, any amplitude of an acquired CAP is, in general, a summation of individual action potentials from the different axons. In particular, if the distance between an energy delivery or activation site and an acquisition site is small, then conduction velocity differences have little opportunity to distribute the response. Another effect concerns phase, i.e., when waves pass an acquisition site in phase they add constructively and display a higher peak. On the other hand, when they are out of phase, they add destructively. Action potentials may travel on a number of peripheral nerve fibers in a manner whereby no CAP can be recorded if they sum destructively or if timing differences do not permit constructive summation, which may be considered if drawing conclusions about nerve "block" based on the amplitude of a CAP.

In general, for a nerve trunk of Aα, Aβ and Aγ fibers only, as stimulus strength is increased, the magnitude of the phase of a monophasic action potential due to Aα fibers increases. However, a further increase in stimulus intensity excites the Aβ fibers to threshold and they now contribute to the compound action potential. Further increasing the stimulus intensity excites more Aα and Aβ fibers and generates a response from Aγ fibers as well. With progressive increases in stimulus intensity, the magnitude of each peak of the monophasic compound action potential eventually reaches a maximal value when all the fibers in the trunk are stimulated to threshold.

A CAP, unlike an intracellularly recorded action potential, it is not an all-or-none response and, unlike an intracellularly recorded action potential, it does not reflect the activity of a single nerve cell; rather, it reflects the sum of the activity of all the cells in the trunk that have been excited.

Figure 4:
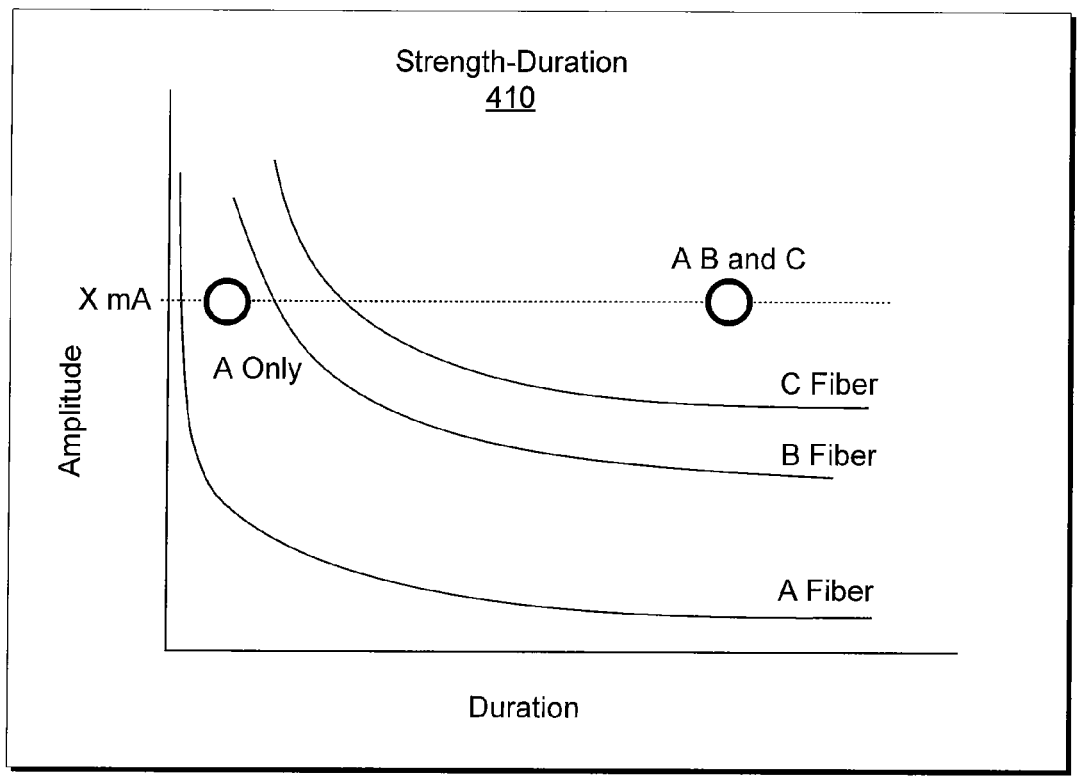
FIG. 4 is a plot of strength and duration for nerve activation and a plot of frequency with respect to nerve activation.
Figure 4:
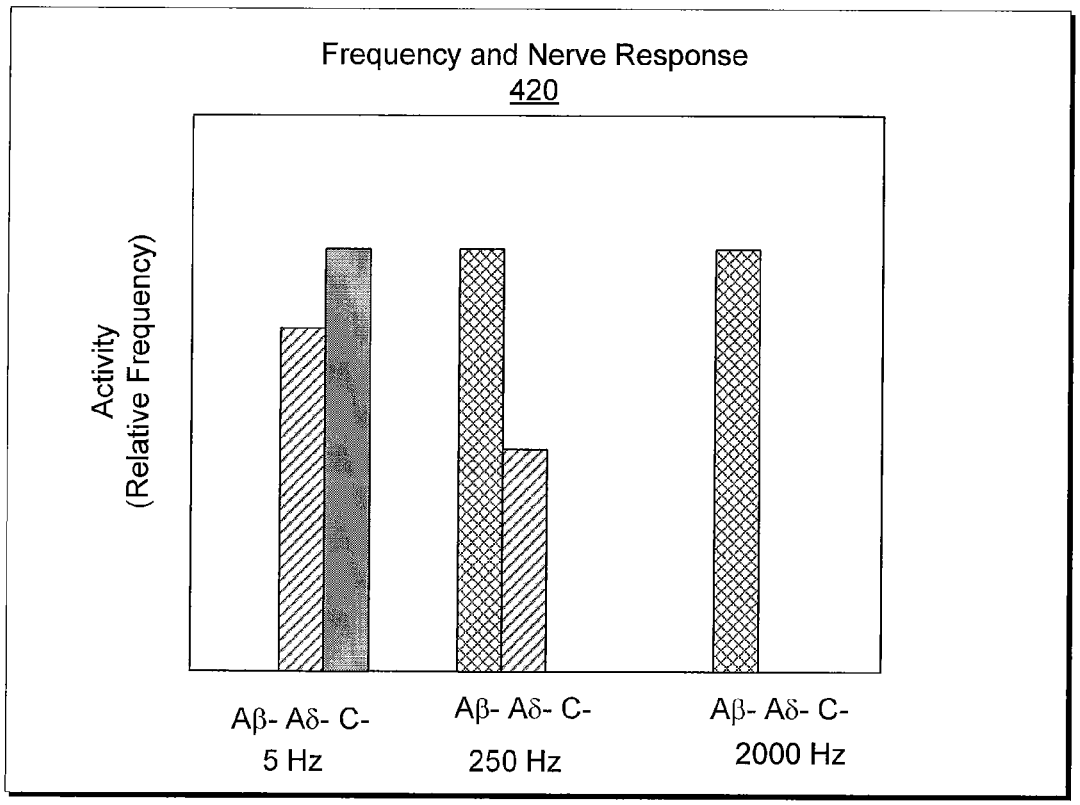

FIG. 4 shows a strength-duration plot 410 and an activation frequency plot 420 for various types of nerve fibers. Such information may be used to tailor delivery of energy to a nerve and/or to analyze acquired information.

The strength-duration plot 410 includes a curve for A fibers, a curve for B fibers and a curve for C fibers. Below a curve, the particular combination of energy amplitude and duration will not elicit an action potential, referred to herein as an evoked response. In the plot 410, a dashed line represents a constant amplitude of X mA. Two points are identified, one for a short duration and one for a longer duration. At the short duration, only A fibers will produce an evoked response whereas at the longer duration, A, B and C fibers will produce an evoked response. Hence, various exemplary methods may include delivering energy to a nerve at more than one strength-duration to selectively activate different populations and/or types of nerve fibers.

The frequency and nerve response plot 420 demonstrates how the frequency of the energy delivered to a nerve may affect response. This particular example pertains to afferent fibers. In general, there are three types of sensory afferent fibers that send sensory information to the central nervous system; unmyelinated C fibers send a long lasting delayed painful sensation, thinly myelinated Aδ fibers send a short and fast painful sensation and the thickly myelinated Aβ fibers send tactile information.

A study by Koga et al., "Selective activation of primary afferent fibers evaluated by sine-wave electrical stimulation", *Molecular Pain* 2005, I:13, reported electrophysiological properties of various fibers in the dorsal root ganglion. Table 2 shows resting membrane potential (RMP), conduction velocity (CV), threshold of stimulus intensity (TSI) and duration of action potential (APD) at half maximum amplitude for C fibers, Aδ fibers and Aβ fibers.

TABLE 2

Electrophysiological Properties

|  | RMP (mV) | CV (m/s) | TSI (mA) | APD (ms) |
|---|---|---|---|---|
| C fibers | −63.0 | 0.6 | 3.1 | 1.38 |
| Aδ fibers | −67.7 | 5.9 | 1.8 | 0.63 |
| Aβ fibers | −65.1 | 19.6 | 0.8 | 0.29 |

The plot 420 of FIG. 4 shows results from the study of Koga et al., which indicate that pulses at 2000 Hz stimulate large myelinated (Aβ) fibers, pulses at 250 Hz stimulate large myelinated (Aβ) fibers and small myelinated (Aδ) fibers and pulses at 5 Hz stimulate small unmyelinated (C) fibers and small myelinated (Aδ) fibers. Hence, various exemplary methods may include delivering energy to a nerve at more than one frequency to selectively activate different populations and/or types of nerve fibers.

An exemplary method may include delivering energy to a nerve at more than one frequency and/or at more than one strength-duration to selectively activate different populations and/or types of nerve fibers.

Figure 5:
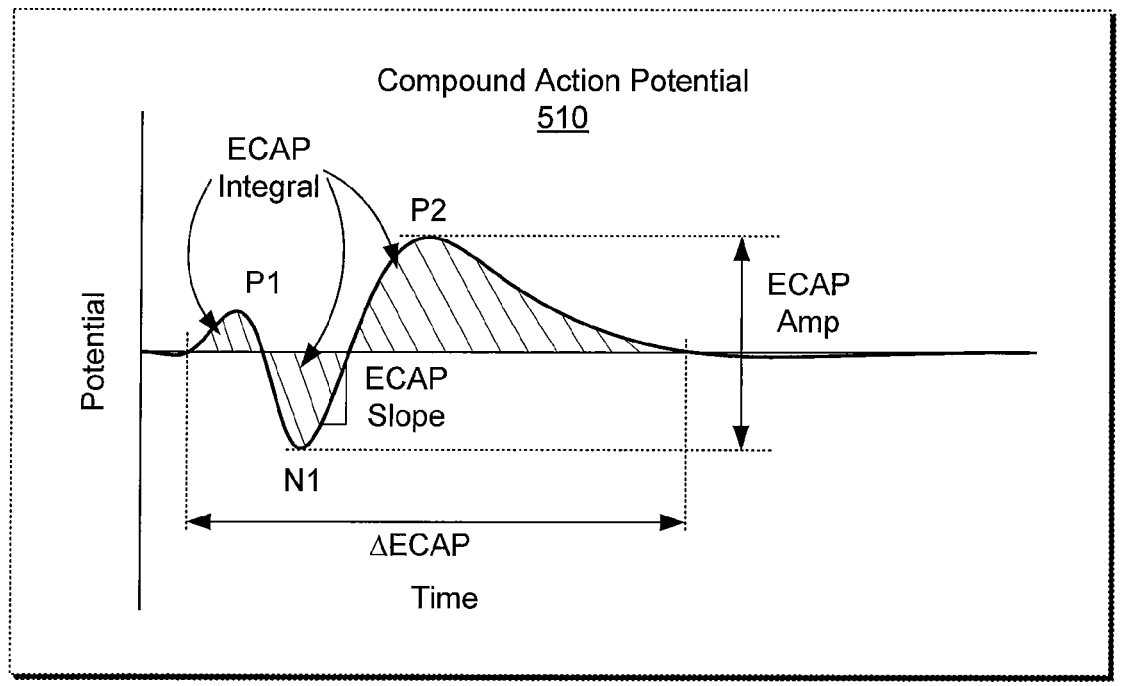
FIG. 5 is a plot of a compound action potential and various characteristics that may be used to help assess nerve condition and a plot of compound action potential versus activation energy along with a nerve response technique.
Figure 5:
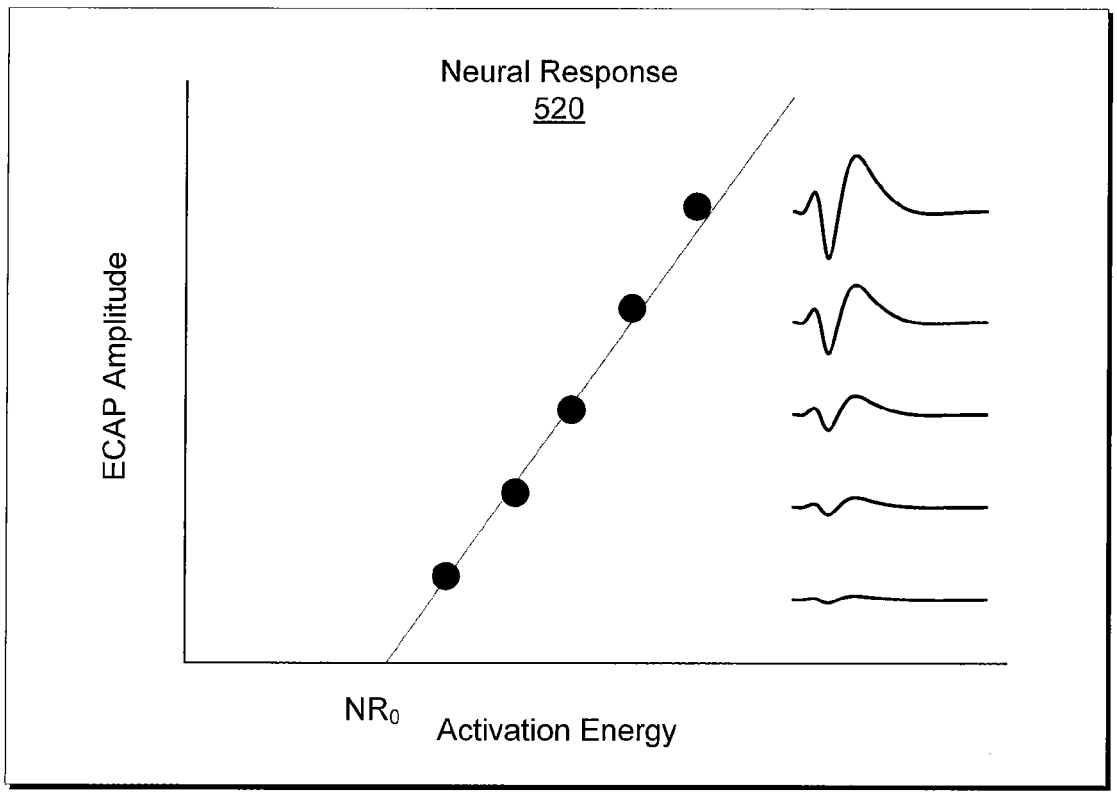

FIG. 5 shows a single CAP 510 and various characteristics that may be used to analyze a CAP. Such a CAP may be an evoked response or an evoked CAP (ECAP). A typical electrically elicited CAP (ECAP) includes a triphasic waveform with a small positive peak (P1) followed by a negative trough (N1) followed by a positive peak (P2). The latency of the CAP (e.g., time between stimulus onset and the onset of P1) is typically about 100 μs to about 300 μsec. The amplitude of the ECAP is typically defined as the absolute difference (in μvolts) between N1 and P2. This amplitude usually increases with the magnitude of the activation current because more nerve fibers are contributing to the response as the energy level is increased. Another parameter is maximum slope of the ECAP. Other parameters include, for example, width of a peak at half amplitude, duration (ΔECAP) minimum slope, area (e.g., integral, integral of a phase, etc.), highest frequency component, lowest frequency component, etc. Techniques such as Fourier and/or wavelet analysis may be used to analyze an ECAP to associated activity and nerve type.

As an ECAP is typically multiphasic, any of a variety of parameters may be applied to a single phase or less than all phases. Ratios, subtractions, additions, etc., may be used in analyzing an ECAP. For example, integrals for P1, N1 and P2 may be summed for a total integral or ratios for integrals or amplitudes (e.g., P1/(P1+N1+P2)) may be used to assess nerve condition. Other combinations include, for example, duration of P2 to ΔECAP, area of N1 to ΔECAP, etc.

For increase signal strength of an ECAP, (a) an acquisition electrode should be fairly close to the nerve tissue, (b) a sufficient number of neurons should be firing, and (c) resulting evoked responses should occur closely in time. Thus, the ability to measure a CAP is highly influenced by how many nerve fibers are available to respond, whether those fibers fire synchronously or are in refractory periods, and the fibers' location with respect to the signal acquisition electrode or electrodes.

A procedure known as neural response imaging (NRI) is used for measuring auditory nerve responses from the cochlea (Han et al., "Comparisons between neural response imaging thresholds, electrically evoked auditory reflex thresholds and most comfortable loudness levels in CII bionic ear users with HiResolution sound processing strategies", *Acta Otolaryngol.* 2005 July; 125(7):732-5). This procedure uses electrodes implanted on the auditory nerve to deliver energy at various levels and to measure evoked responses for programming the cochlear implants of young children who cannot demonstrate a reliable judgment of loudness. Specifically, the procedure delivers stimuli at different energy levels, records ECAP amplitude and then determines a base value referred to as tNRI.

FIG. 5 shows a plot 520 to illustrate a procedure that may be used by an exemplary method to assess nerve condition. The procedure includes delivering energy to a nerve at a plurality of energy levels and determining an amplitude for each evoked CAP and then analyzing the amplitude information as a function of energy. Such analyzing may include determining a base value $NR_0$ that corresponds to a null amplitude CAP. An exemplary method may include using such a procedure over time to investigate trends that may help to assess nerve condition. For example, values for $NR_0$ may be determined at various times and compared to assess nerve condition.

Figure 6:
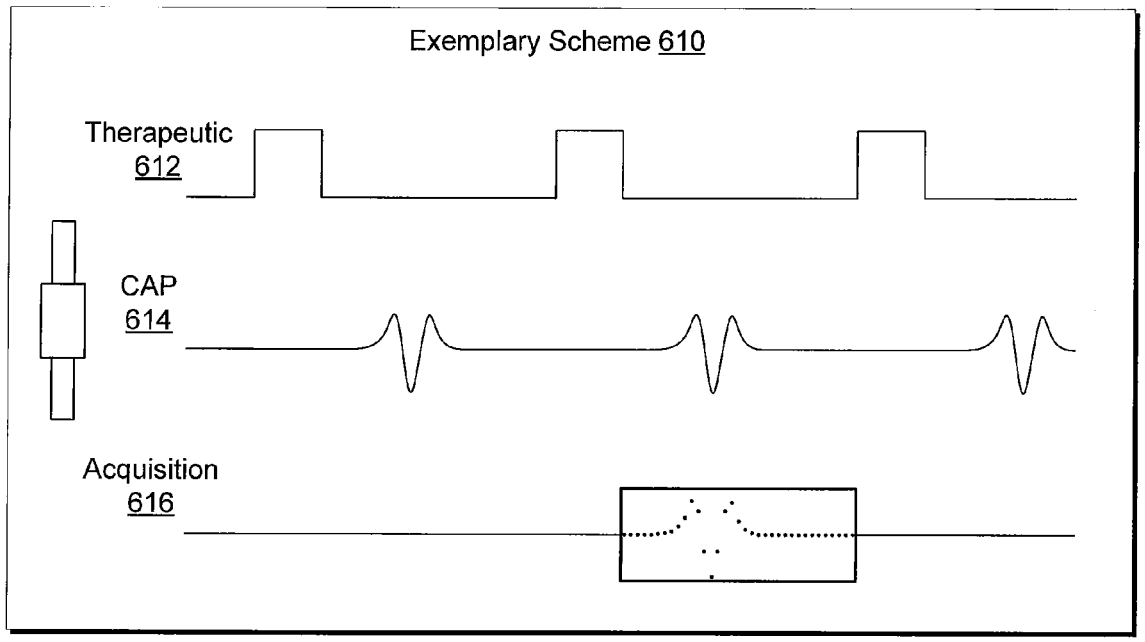
FIG. 6 is a diagram of an exemplary scheme that acquires compound action potential responsive to therapeutic nerve stimulation and an exemplary scheme that acquires compound action potential responsive to diagnostic nerve stimulation.
Figure 6:
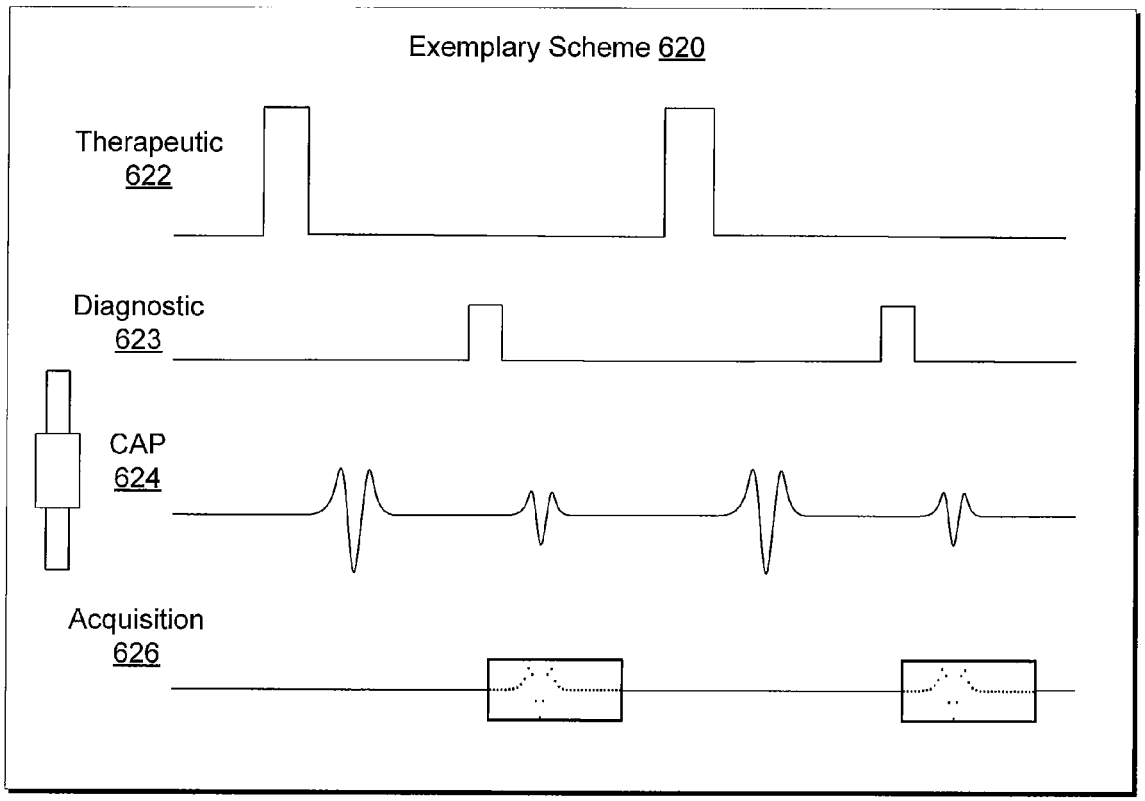

FIG. 6 shows two exemplary schemes 610, 620 for acquiring CAPs. The scheme 610 includes delivering therapeutic stimulation energy 612 to a nerve, for example, using square wave pulses at periodic intervals. In general, each of these pulses evokes a compound action potential as indicated by the CAPs 614. Control logic may implement a sensing window to acquire one or more of these ECAPs 616. In the example of FIG. 6, the control logic implements the sensing window according to a schedule, a counter, a set period, etc., where less than all ECAPs are sensed. The exemplary scheme 610 requires one or more electrodes to acquire ECAPs responsive to therapeutic nerve stimulation.

The scheme 620 includes delivering therapeutic stimulation energy to a nerve 622 and delivering diagnostic stimulation energy to a nerve 623. In the instance where the same nerve receives the therapeutic and the diagnostic energy, these energies may evoke CAPs 624. However, as shown, the acquisition or sensing window 626 acquires ECAPs responsive to the diagnostic energy only. In this scheme, diagnostic refers to energy delivered for purposes of assessing nerve condition. The diagnostic energy and the therapeutic energy may be delivered using at least one common electrode or completely different electrodes. Acquisition of ECAPs may use at least one electrode that is used for delivery of diagnostic energy (e.g., a common ground electrode) and/or therapeutic energy, alternatively, acquisition of ECAPs may occur using electrodes that are not used for delivery of therapeutic energy or diagnostic energy.

Figure 7:
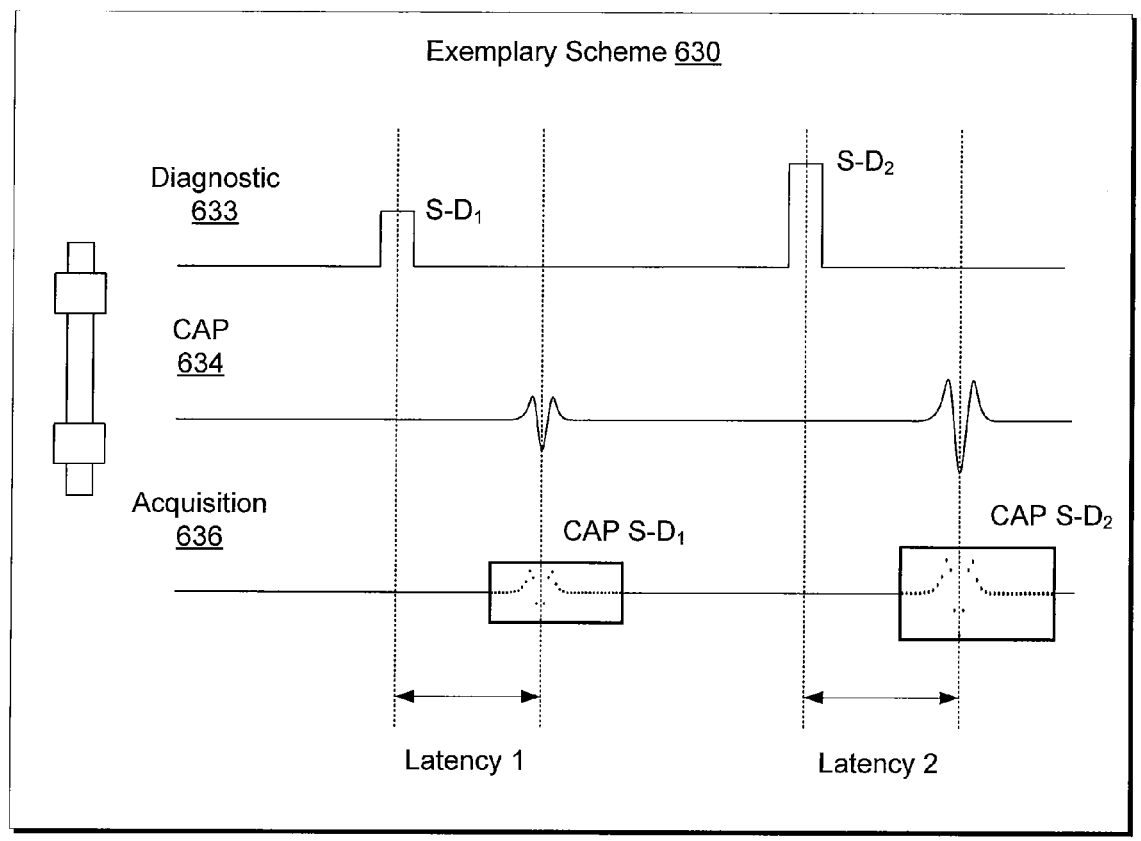
FIG. 7 is a diagram of an exemplary scheme that acquires compound action potentials responsive to energy delivered using different delivery parameters.

FIG. 7 shows another exemplary scheme 630 where latency of an ECAP may be determined. The scheme 630 includes delivering diagnostic energy to a nerve 633 using at least two different sets of energy delivery parameters. The example of FIG. 7 shows delivery of diagnostic energy using a first strength-duration (S-$D_1$) and delivery of diagnostic energy using a second strength-duration (S-$D_2$). As explained with respect to FIG. 3, strength-duration may be used to activate certain populations of nerve fibers within a nerve trunk. Thus, the pulse S-$D_1$ may aim to avoid activation of B and C fibers while the pulse S-$D_2$ may activate A, B and C fibers. In this example, or other examples, parameters such as frequency, location, etc., may differ between energy delivery parameter sets. Further, while various pulses are shown as square waves, biphasic or other waveforms may be used for delivery of therapeutic energy and/or diagnostic energy to a nerve.

The example of FIG. 7 includes delivery of energy at one site and acquisition of an ECAP at another site and shows two ECAPs 634 and two acquisition windows 636 where a first ECAP and window correspond to the S-$D_1$ pulse and a second ECAP and window correspond to the S-$D_2$ pulse. In this example, a first and a second latency are shown, which may be analyzed for purposes of assessing nerve condition. More particularly, the distance between the energy delivery site and the ECAP acquisition site are known as well as the time of the energy delivery, hence, latency may be determined along with conduction velocity for each of S-$D_1$ and S-$D_2$.

As explained with respect to Tables 1 and 2, conduction velocity can differ depending on fiber type. For example, a conduction velocity of 100 m/s could only have arisen from a type A fiber while a slower conduction velocity may be associated with a different type of fiber (e.g., or a damaged A fiber). Depending on the nature of peak identification, conduction velocity may be an average of the conduction velocities of individual fibers contributing to a peak. In general, every peak is broad (spread out along the time axis) because not all fibers of a particular type have exactly the same conduction velocity.

As explained with respect to plot 520 of FIG. 5, an increase in energy can cause an increase in ECAP amplitude. Hence, the exemplary scheme 630 may be used to determine a relationship between diagnostic energy and ECAP amplitude (noting that a relationship between therapeutic energy, where applied, and ECAP amplitude may also be determined).

Figure 8:
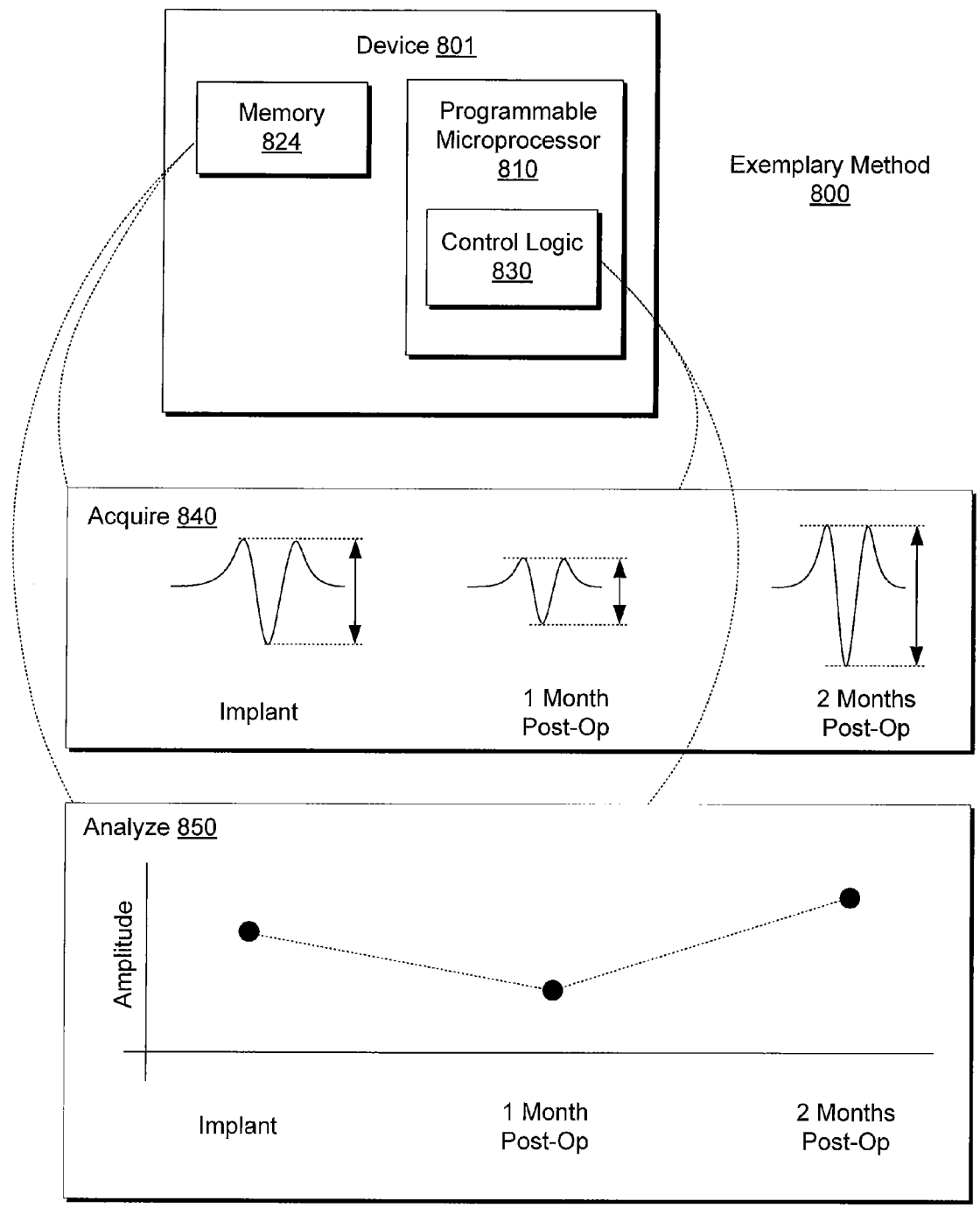
FIG. 8 is a diagram of an exemplary method for acquisition of compound action potentials and analysis of such potentials.

FIG. 8 shows an exemplary method 800 for assessing nerve condition. The method 800 includes acquiring two or more ECAPs 840 and analyzing the acquired ECAPs 850. The method 800 is illustrated in conjunction with an exemplary device 801, which may be an implantable device or a device in communication with an implantable device. The device 801 includes a programmable microprocessor 810, control logic 830 and memory 824. The control logic 830 may be in the form of instructions stored on a digital data storage medium accessible by the processor 810 where the instructions cause the processor to perform various actions. The device 801 may include any of the various features of the device 200 of FIG. 2, the programmer 1330 of FIG. 13 or the computing device 1340 of FIG. 13.

The acquisition block 840 includes acquiring a series of ECAPs, which may include sampling an entire ECAP, a portion of an ECAP or one or more characteristics of an ECAP. In the example of FIG. 8, the acquisition block 840 acquires ECAP amplitude for a series of three ECAPs spaced at one month intervals. The analysis block 850 includes plotting the ECAP amplitudes versus time along with relevant information associated with the time of acquisition for each of the ECAPs. More specifically, the first ECAP corresponds to time of implant of a device such as an electrode (e.g., a wrap, a cuff, etc.) that contacts a nerve, the second ECAP corresponds to a time of one month after implant and the third ECAP corresponds to a time of two months after implant. The plot of the analysis block 850 allows a care provider to assess nerve condition. Such information may also be used by an algorithm that may assess nerve condition.

As already mentioned, a decrease in ECAP amplitude can indicate nerve injury. Thus, the data of the analysis block 850 indicates that nerve condition deteriorated during the first month after implant (i.e., 1 month post-op) and then improved after the subsequent month (i.e., 2 months post-op).

In general, peripheral nerves have an ability to heal. This ability is especially pronounced in cases where the perineural and endoneural tissues (see, e.g., FIG. 3) are preserved such as is the cases during mechanical stress induced by surgery or an improperly placed implant. Thus, the method 800 of FIG. 8, as well as various other exemplary methods, allow for tracking recovery of a nerve or nerves.

An exemplary computing device (e.g., a device programmer) may request and receive information from an implantable device (e.g., acquire information such as the information of block 840) and then analyze the information (e.g., such as the analysis of block 850) to provide a graphical output (e.g., GUI, print out, etc.) that allows a clinician to assess nerve condition.

Figure 9:
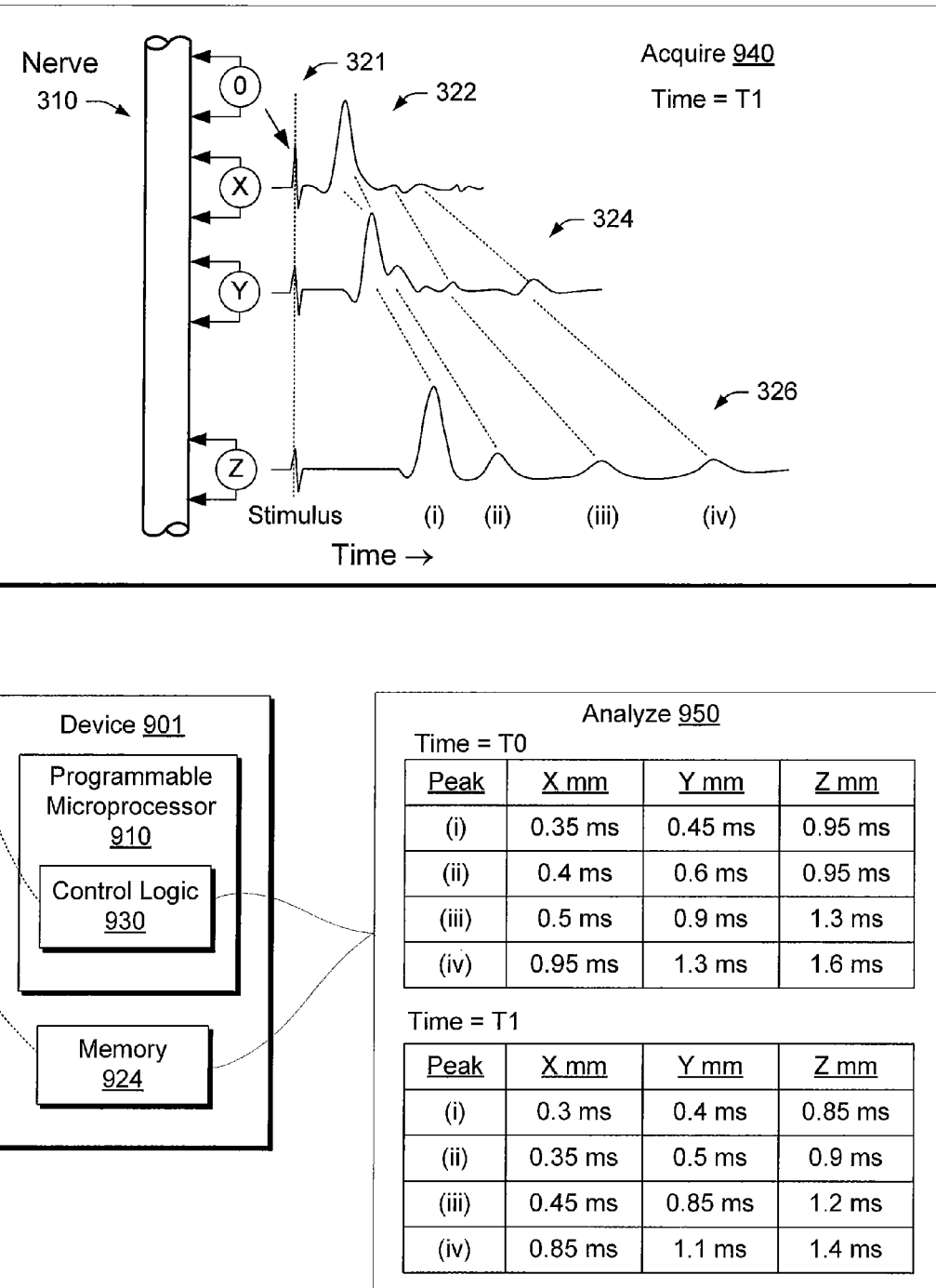
FIG. 9 is a block diagram of an exemplary method for acquisition of compound action potentials and analysis of such potentials.

FIG. 9 shows an exemplary method 900 that includes acquiring ECAP information 940 and analyzing ECAP information 950. The method 900 is illustrated in conjunction with an exemplary device 901, which may be an implantable device or a device in communication with an implantable device, and in conjunction with ECAP information such as that presented in FIG. 3 (e.g., nerve 310, energy 321, ECAPs 322, 324 and 326). The device 901 includes a programmable microprocessor 910, control logic 930 and memory 924. The control logic 930 may be in the form of instructions stored on a digital data storage medium accessible by the processor 910 where the instructions cause the processor to perform various actions. The device 901 may include any of the various features of the device 200 of FIG. 2, the programmer 1330 of FIG. 13 or the computing device 1340 of FIG. 13.

The acquisition block 940 includes acquiring a series of ECAPs, which may include sampling an entire ECAP, a portion of an ECAP or one or more characteristics of an ECAP. More specifically, ECAPs are acquired from one or more sites along a nerve responsive to delivery of energy. The site of energy delivery may be the same for all of the acquired ECAPs and the ECAPs may be responsive to the same stimulus. For example, in FIG. 9, site "0" represents a site for delivery of energy while sites "X", "Y" and "Z" represent other sites where ECAPs may be acquired. Distances between site 0 and sites X, Y and Z may be known (e.g., X mm, Y mm and Z mm) and used for analyzing acquired ECAP information. Latency (e.g., time between site 0 and another site) may be used as a relative indication of nerve demyelination and/or other nerve condition.

An exemplary method may delivery energy at site 0 and then acquire ECAP information at one or more sites or an exemplary method may delivery energy at site 0 and then acquire ECAP information at one site, deliver energy at site 0 and then acquire ECAP information at another site, etc. While this latter example uses one energy delivery site and multiple acquisition sites, another example may use one acquisition site and multiple energy delivery sites. Thus, depending on delivery and acquisition technique, a method may acquire ECAP information for overlapping segments of a nerve and/or separate segments of a nerve.

The acquisition block 940 indicates an acquisition time of T1. The analysis block 920 shows ECAP information for time T1 along with ECAP information for time T0 (e.g., implant time), which represents a time earlier that T1 (e.g., post-implant time). More specifically, in the example of FIG. 9, the ECAP information includes latencies for conduction from site 0 to sites X, Y and Z. Further, various peaks have been identified and a latency is given for each peak, where possible, for example, depending on acquisition and/or analysis techniques (noting that peaks may overlap for one site yet be distinct for another site). The ECAP information of the analysis block 950 may be used to assess nerve condition and may optionally be used to assess nerve condition with respect to nerve fiber type (e.g., where the peaks correspond to different fiber types). Hence, injury and/or recovery may be specific to a particular type or types of nerve fiber.

Figure 10:
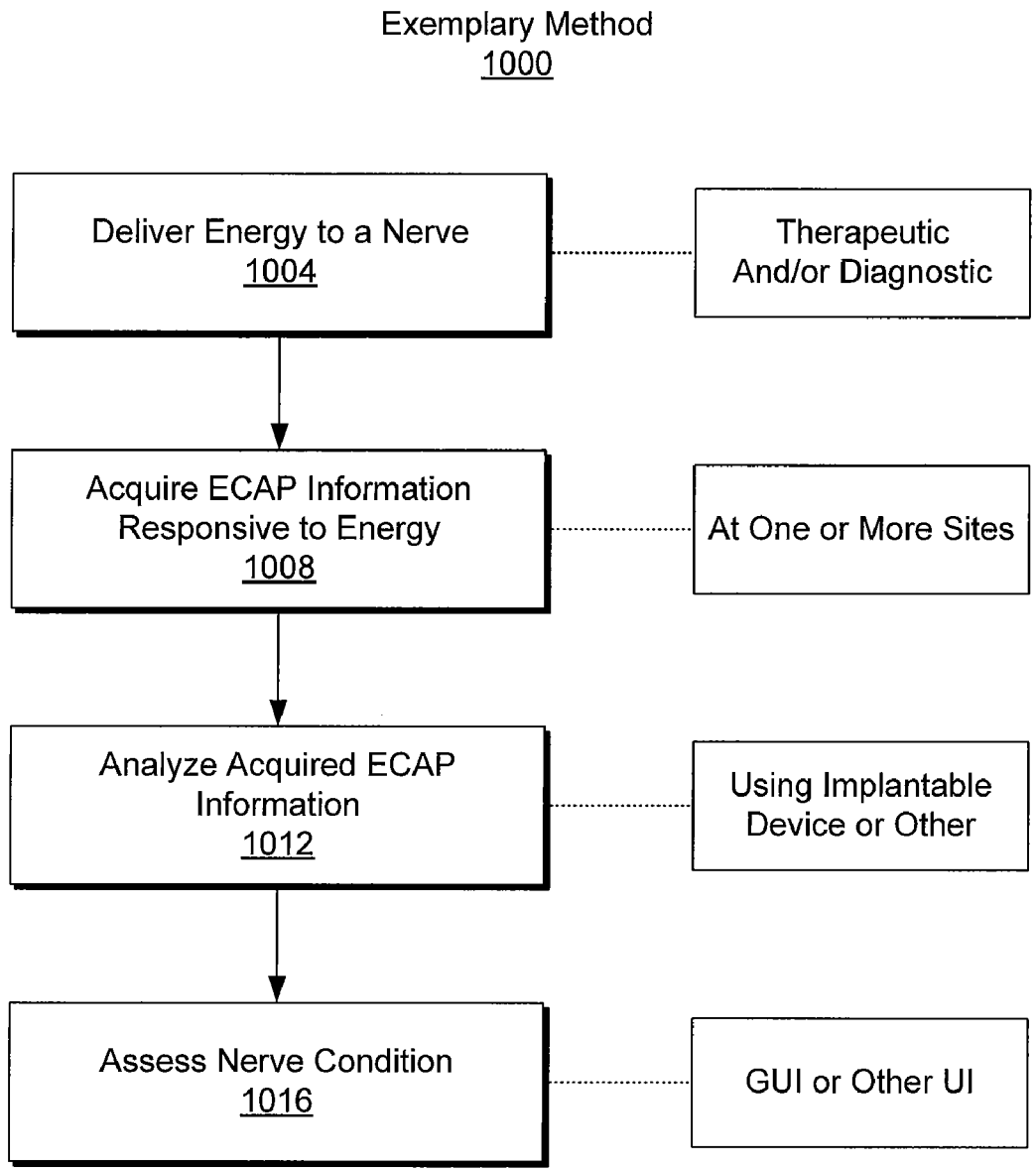
FIG. 10 is a block diagram of an exemplary method for acquisition of compound action potentials and analysis of such potentials.

FIG. 10 shows an exemplary method 1000 for assessing nerve condition. The method 1000 commences in a delivery block 1004 that delivers energy to a nerve. The energy may be therapeutic energy associated with implementation of a nerve stimulation therapy or diagnostic energy for the purpose of diagnosing nerve condition. An acquisition block 1008 acquires ECAP information responsive to the delivered energy. The acquisition may occur at one or more sites (see, e.g., the example of FIG. 9).

Figure 13:
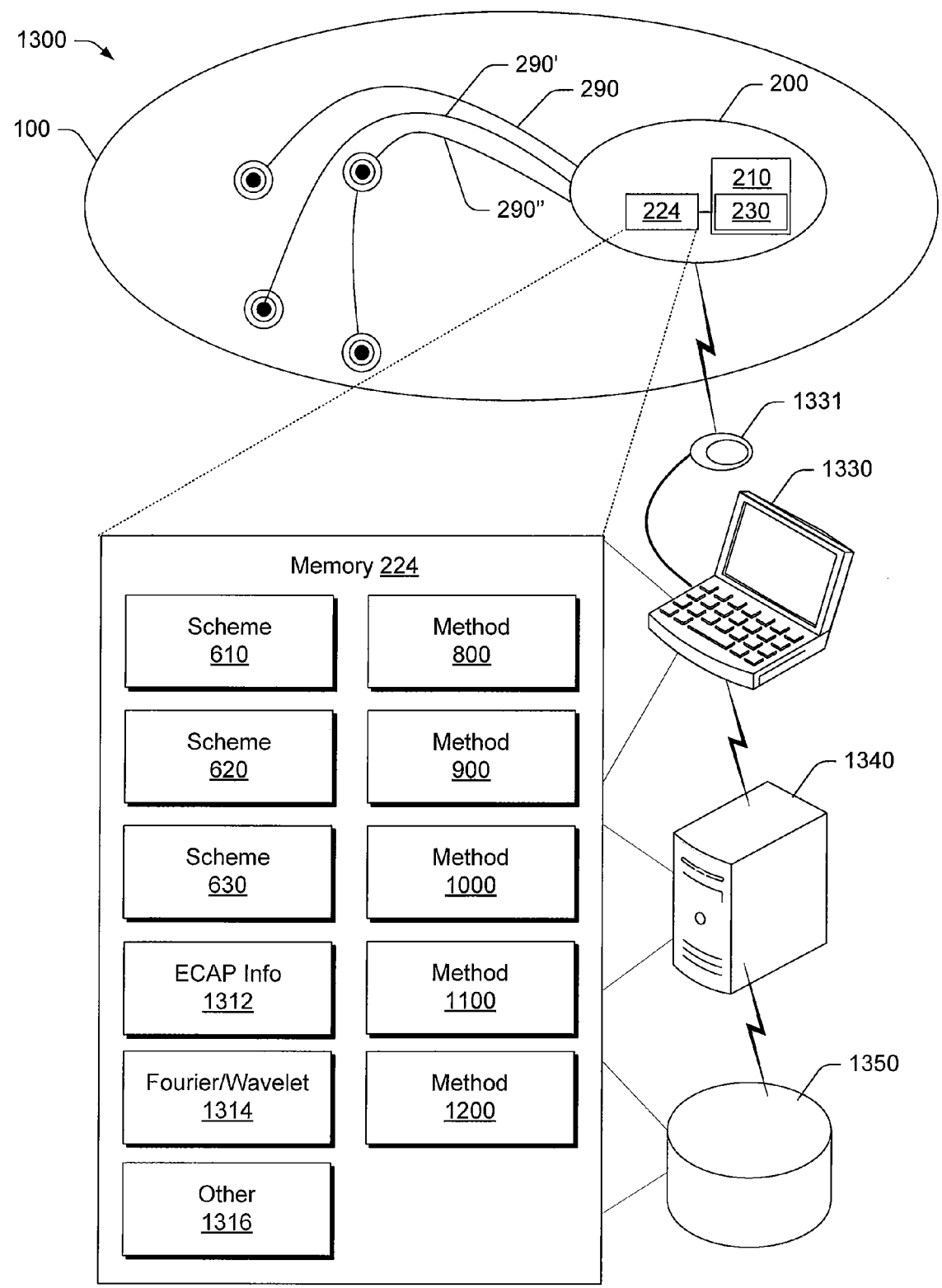
FIG. 13 is a diagram of an exemplary system that includes an implantable device for acquiring compound action potentials and various external devices that may analyze such potentials and/or provide for assessment of nerve condition.

An analysis block 1012 analyzes the acquired ECAP information, optionally in conjunction with previously acquired or analyzed ECAP information. Such an analysis may occur using an implantable device and/or an external device. For example, FIG. 13 shows an implantable device 200 in communication with an external device 1330. In this example, analyzing may occur solely on the implantable device 200, solely on the external device 1330 or on a combination of the implantable device 200 and the external device 1330.

An assessment block 1016 presents information to a clinician using analyzed ECAP information. The information may be presented in the form of a graph, a table, an alert (buzzer, phone message, etc.) or other user interface. A clinician may optionally adjust one or more operational parameters of a therapeutic and/or a diagnostic process based at least in part on such presented information. For example, the device 1330 may be capable of programming the implantable device 200 using a graphic user interface that presents nerve assessment information and control buttons, fields, etc. Hence, an exemplary GUI may present nerve assessment information and options for controlling an implantable device on a single GUI or a series of related and linked GUI (e.g., linked via software instructions).

An exemplary method may include implementing a nerve stimulation therapy that includes delivering stimulation energy to a target nerve (e.g., therapeutic and/or diagnostic), periodically acquiring compound action potentials responsive to the delivered stimulation energy and assessing condition of the target nerve based at least in part on the periodically acquired compound action potentials. Such a method may acquire a compound action potential responsive to every delivery of stimulation energy. Such a method may include a vagal nerve as a target nerve. According to such a method, nerve stimulation therapy may treat epilepsy by delivering therapeutic stimulation energy to a vagal nerve, treat obesity by delivering therapeutic stimulation energy to a vagal nerve, or treat sleep apnea by delivering therapeutic stimulation energy to a phrenic nerve. A method may determine if condition of the target nerve is worsening or improving.

An exemplary method may include periodically delivering diagnostic stimulation energy to a target nerve (see, e.g., scheme 620 of FIG. 6 and scheme 630 of FIG. 7), periodically acquiring compound action potentials responsive to the periodically delivered diagnostic stimulation energy and assessing condition of the target nerve based at least in part on the periodically acquired compound action potentials.

Figure 11:
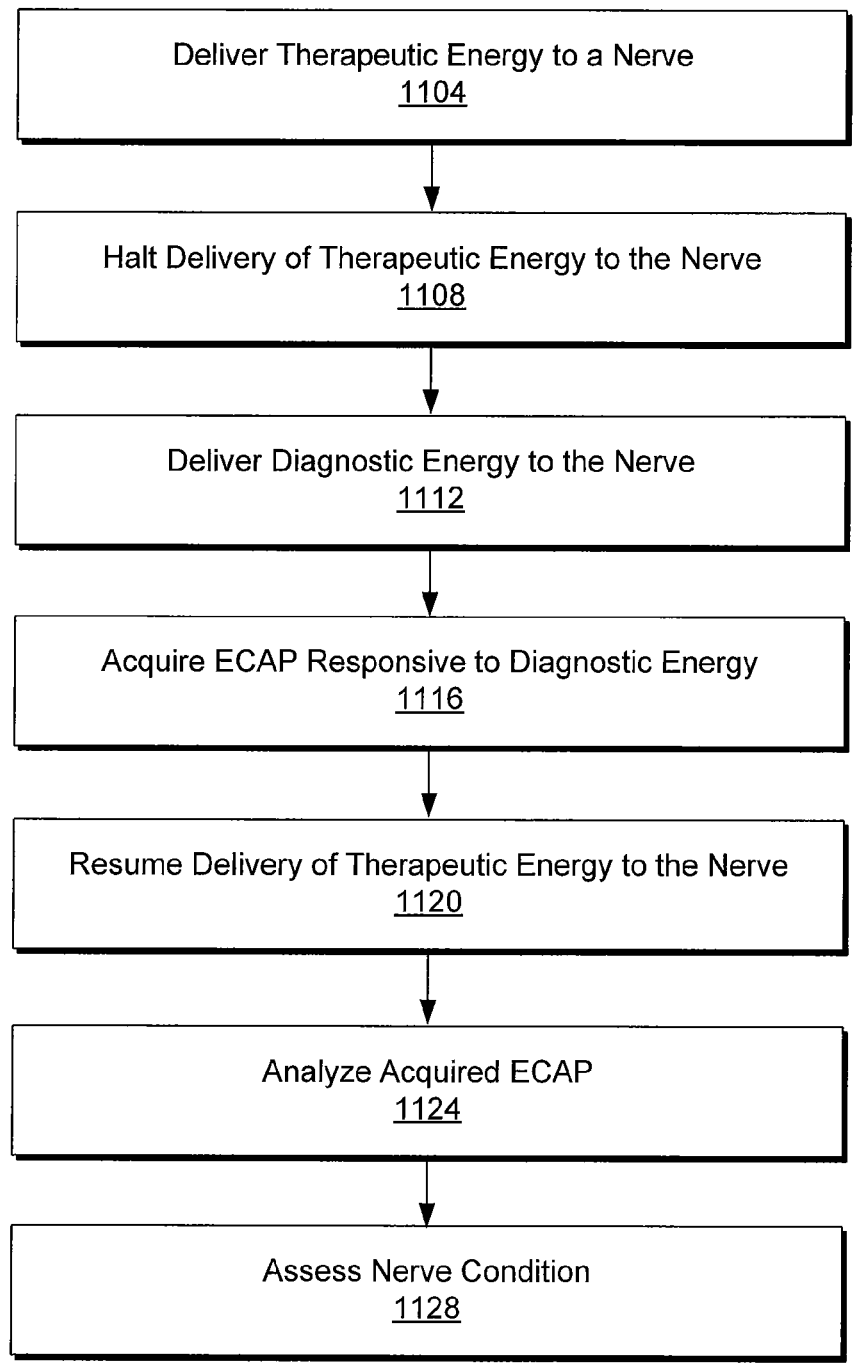
FIG. 11 is a block diagram of an exemplary method for acquisition of compound action potentials and analysis of such potentials.

FIG. 11 shows an exemplary method 1100 for assessing nerve condition. The method 1100 commences in a delivery block 1104 that delivers therapeutic energy to a nerve. A subsequent block 1108 halts delivery of the therapeutic energy to the nerve such that another delivery block 1112 can delivery diagnostic energy to the nerve and such that an acquisition block 1116 can acquire ECAP information responsive to the delivered diagnostic energy without interference from the therapeutic energy. Once the diagnostic delivery and ECAP acquisition cycle or loop has occurred, then a block 1120 calls for the delivery of the therapeutic energy to the nerve to resume.

An analysis block 1124 analyzes the acquired ECAP information and an assessment block 1128 may present results of the analysis to a clinician to thereby allow a clinician to assess condition of the nerve. In an alternative example, an implantable device or external device may assess nerve condition and act accordingly. For example, a device may halt delivery of therapeutic energy based on nerve condition, especially where nerve condition impairs delivery of therapeutic energy or the intended effect of the therapeutic energy. While the various action blocks are shown in a particular order, for example, the blocks 1124 and/or 1128 may occur prior to the block 1120. Hence, in this example, the assessment may control resumption of the therapeutic nerve stimulation.

An exemplary method may include implementing a nerve stimulation therapy that includes delivering therapeutic stimulation energy to a target nerve; temporarily halting the delivering therapeutic stimulation energy to the target nerve; during the halting, delivering diagnostic stimulation energy to the target nerve; acquiring a compound action potential responsive to the delivered non-therapeutic stimulation energy; recommencing the delivering therapeutic stimulation energy to the target nerve; and assessing condition of the target nerve based at least in part on the acquired compound action potential. Such a method may deliver energy to a vagal nerve. Such a nerve stimulation therapy may treat epilepsy by delivering therapeutic stimulation energy to a vagal nerve, treat obesity by delivering therapeutic stimulation energy to a vagal nerve, or treat sleep apnea by delivering therapeutic stimulation energy to a phrenic nerve. With respect to nerve condition, an assessment may determine if condition of the target nerve is worsening or improving.

An exemplary method may include implementing a nerve stimulation therapy that includes periodically delivering therapeutic stimulation energy to a target nerve; periodically delivering diagnostic stimulation energy to the target nerve where the delivering therapeutic stimulation energy and the delivering non-therapeutic stimulation energy occur asynchronously; periodically acquiring compound action potentials responsive to the periodically delivered diagnostic stimulation energy; and assessing condition of the target nerve based at least in part on the periodically acquired compound action potentials.

Figure 12:
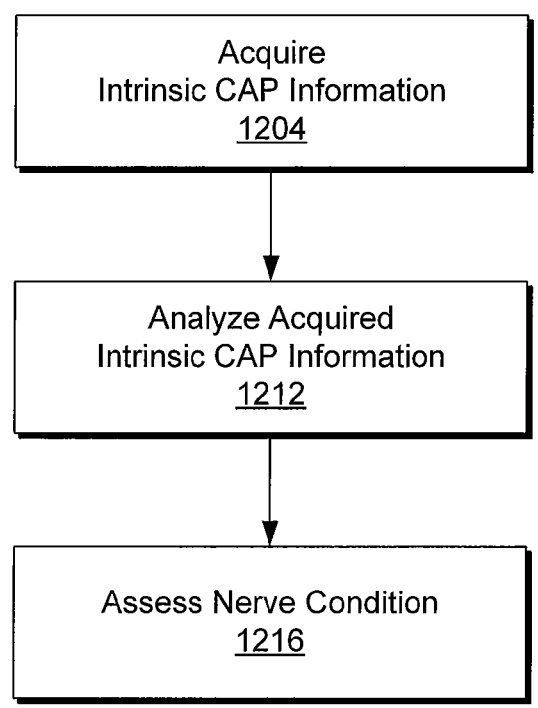
FIG. 12 is a block diagram of an exemplary method for acquisition of intrinsic compound action potentials and analysis of such potentials.

FIG. 12 shows an exemplary method 1200 for assessing nerve condition based on intrinsic activity. The method 1200 commences in an acquisition block 1204 that acquires intrinsic CAP information, as may occur to a normally occurring physiologic stimulus as contrasted to energy delivered to a nerve using an implantable device. The acquisition may occur at one or more sites (see, e.g., the example of FIG. 9). An analysis block 1212 analyzes the acquired intrinsic CAP information, optionally in conjunction with previously acquired or analyzed ECAP information and/or intrinsic CAP information. Such an analysis may occur using an implantable device and/or an external device. For example, FIG. 13 shows an implantable device 200 in communication with an external device 1330. In this example, analyzing may occur solely on the implantable device 200, solely on the external device 1330 or on a combination of the implantable device 200 and the external device 1330.

An assessment block 1216 presents information to a clinician using at least the analyzed intrinsic CAP information. The information may be presented in the form of a graph, a table, an alert (buzzer, phone message, etc.) or other user interface. A clinician may optionally adjust one or more operational parameters of a therapeutic and/or a diagnostic process based at least in part on such presented information. For example, the device 1330 may be capable of programming the implantable device 200 using a graphic user interface that presents nerve assessment information and control buttons, fields, etc. Hence, an exemplary GUI may present nerve assessment information and options for controlling an implantable device on a single GUI or a series of related and linked GUI (e.g., linked via software instructions).

An exemplary method may include monitoring intrinsic nerve activity and deriving one or more numerical parameters based at least in part on acquired intrinsic nerve activity data. For example, a maximum amplitude of nerve activity may be acquired over a pre-determined period (e.g., 24 hours, etc.) and/or a distribution of nerve activity amplitudes may be acquired continuously or over a pre-determined period (e.g., 24 hours, etc.). Such information may be used to assess nerve condition. For example, if the maximum amplitude diminishes over a course of several months or more abruptly then a clinician may more accurately diagnose a mechanism of nerve deterioration. In turn, a therapy may be adjusted, a drug prescribed, etc.

With respect to acquisition of nerve activity information (e.g., nerve activity data), one or more triggers may be used. For example, a device may monitor amplitude of nerve activity and trigger acquisition of nerve activity information if amplitude exceeds an amplitude limit, which may be set by any of a variety of techniques (e.g., entered as a value or determined based on acquired nerve activity data such as a standard deviation of averaged samples). In another example, triggering is based on analyzed information such as a change in a fast Fourier transform analysis of nerve activity data, etc.

As described herein, an exemplary method may include monitoring intrinsic compound action potentials for a target nerve for a period of time using an implantable device, determining a maximum amplitude for the intrinsic compound action potentials for the period of time and assessing condition of the target nerve based at least in part on the maximum amplitude where such an assessment may determine if condition of the target nerve is worsening or improving. For example, an injury to a nerve may worsen or improve over time or a disease may cause nerve condition to deteriorate while a therapy that treats the disease or its causes may improve nerve condition.

An exemplary method may include monitoring intrinsic nerve activity for a target nerve using an implantable device, determining if amplitude for one of the intrinsic nerve activity exceeds an amplitude limit, if amplitude exceeds the amplitude limit, triggering acquisition of nerve activity data using the implantable device and assessing condition of the target nerve based at least in part on the acquired nerve activity data.

An exemplary method may include acquiring intrinsic compound action potential information for a target nerve using an implantable device, analyzing the acquired compound action potential information using a fast Fourier transform analysis (FFT) and assessing condition of the target nerve based on the analysis.

FIG. 13 shows an exemplary system 1300 that includes the exemplary implantable device 200 of FIG. 2, with processor 210 including one or more modules 230, for example, that may be loaded via memory 224. A series of leads 290, 290' and 290" provide for delivery of stimulation energy and/or sensing activity, etc., associated with the nervous system of the body 100. Other arrangements are possible and may a system may include leads, electrodes, sensors, etc., for other purposes (e.g., cardiac pacing therapy, etc.).

Memory 224 is shown as including appropriate modules (e.g., processor-executable instructions) for performing various actions of the schemes or methods 610, 620, 630, 800, 900, 1000, 1100, 1200, etc., noting that part of a method may be performed using a device other than the implantable device 200. Memory 224 may be considered a computer-readable medium.

The system 1300 includes a device programmer 1330 having a telemetry unit 1331 for communicating with the implantable device 200. The programmer 1330 may further include communication circuitry for communication with another computing device 1340, which may be a server. The computing device 1340 may be configured to access one or more data stores 1350, for example, such as a database of information germane to a patient, an implantable device, therapies, diagnostics, etc.

Devices 200, 1330, 1340 and 1350 of the system 1300 may include one or more computer-readable media with processor-executable instructions for performing one or more actions of the schemes or methods 610, 620, 630, 800, 900, 1000, 1100, 1200, etc. A module or instructions may be the basis for control logic, which may direct hardware and/or software (see, e.g., control logic 830 of FIG. 8). For example, instructions embodied in a computer-readable medium of the programmer 1330 may cause the telemetry unit 1331 to acquire information from the implantable device 200, to analyze such information and to display acquired and/or analyzed information to a display 1332 of the programmer 1330.

Memory 224 of the implantable device 200 or the other devices may store CAP and/or ECAP information (raw or analyzed) 1312 and may include algorithms for analysis such as Fourier and/or wavelet analysis 1314. Other modules may also be included 1316.

With respect to Fourier analysis, such a technique may be used to analyze a CAP and/or an ECAP. For example, Fourier analysis may be used to break an ECAP into components based on frequency. In particular, Fourier analysis may be used to transform information in a time domain to information in a frequency domain. Such an analysis may be used to assess nerve condition and optionally to determine nerve type in association with nerve condition.

With respect to wavelet analysis, a wavelet is a waveform of effectively limited duration that has an average value of zero. A comparison may be made between wavelets and sine waves, the latter of which are the basis of Fourier analysis. In general, sinusoids do not have limited duration—they extend from minus to plus infinity, and where sinusoids are smooth and predictable, wavelets tend to be irregular and asymmetric. Fourier analysis may break a signal into sine waves of various frequencies; wavelet analysis may break a signal into shifted and scaled versions of the original (or mother) wavelet. Signals with sharp changes may be better analyzed with an irregular wavelet than with a smooth sinusoid. In addition, sometimes local features can be described better with wavelets that have local extent.

The programmer 1330 includes a display that may display various information to allow a clinician to assess nerve condition and/or to program an implantable device for acquisition and/or analysis of CAP information and/or ECAP information for purposes of assessing nerve condition. For example, an implantable neurostimulation device may periodically acquire CAP/ECAP information (e.g., peak-to-peak amplitude, latency, etc.) and present the information (raw or analyzed) to a clinician (e.g., as a graphical trend) in a manner that can be interpreted as a measure of the relative health of the nerve being monitored.

An exemplary method may include acquiring peak-to-peak amplitudes for compound action potentials using an implantable neurostimulation device and assessing condition of the target nerve based at least in part on the acquired peak-to-peak amplitudes. In such a method, acquisition of peak-to-peak amplitude(s) may occur periodically, for example, according to a schedule or a trigger.

An exemplary method may include implementing a nerve stimulation therapy that includes delivering stimulation energy to a target nerve using an implantable neurostimulation device, acquiring latency for a compound action potential responsive to the delivered stimulation energy and assessing condition of the target nerve based at least in part on the acquired latency. In such a method, acquisition of latency(ies) may occur periodically, for example, according to a schedule or a trigger. Further, an assessment of condition may use a plurality of latencies.

An exemplary programmer for an implantable device may include a processor, memory, a graphical user interface, a telemetry unit for communicating with an implantable device and control logic to acquire compound action potential information from an implantable device using the telemetry unit and to present the acquired compound action potential information to the graphical user interface for display of a trend in condition of a nerve. Such a programmer may include control logic to analyze the acquired action potential information for one or more trends. Such a programmer may include control logic to analyze the acquired action potential information and to indicate whether condition of a nerve is improving or worsening. For example, the condition may pertain to an injury process or a recovery process of the nerve.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method comprising:
implementing a nerve stimulation therapy within the body that comprises delivering therapeutic stimulation energy to a target nerve;
temporarily halting the delivering therapeutic stimulation energy to the target nerve;
during the halting, delivering diagnostic stimulation energy to the target nerve;
acquiring a compound action potential responsive to the delivered non-therapeutic stimulation energy;
recommencing the delivering therapeutic stimulation energy to the target nerve; and
assessing condition of the target nerve based at least in part on the acquired compound action potential.

2. The method of claim 1 wherein the target nerve comprises a vagal nerve.

3. The method of claim 1 wherein the nerve stimulation therapy treats epilepsy by delivering therapeutic stimulation energy to a vagal nerve.

4. The method of claim 1 wherein the nerve stimulation therapy treats obesity by delivering therapeutic stimulation energy to a vagal nerve.

5. The method of claim 1 wherein the nerve stimulation therapy treats sleep apnea by delivering therapeutic stimulation energy to a phrenic nerve.

6. The method of claim 1 wherein the assessing comprises determining if condition of the target nerve is worsening or improving.

7. A method comprising:
- implementing a nerve stimulation therapy within the body that comprises delivering stimulation energy to a target nerve;
- periodically acquiring compound action potentials responsive to the delivered stimulation energy; and
- assessing condition of the target nerve based at least in part on the periodically acquired compound action potentials.

8. The method of claim 7 wherein the acquiring acquires a compound action potential responsive to every delivery of stimulation energy.

9. The method of claim 7 wherein the target nerve comprises a vagal nerve.

10. The method of claim 7 wherein the nerve stimulation therapy treats epilepsy by delivering therapeutic stimulation energy to a vagal nerve.

11. The method of claim 7 wherein the nerve stimulation therapy treats obesity by delivering therapeutic stimulation energy to a vagal nerve.

12. The method of claim 7 wherein the nerve stimulation therapy treats sleep apnea by delivering therapeutic stimulation energy to a phrenic nerve.

13. The method of claim 7 wherein the assessing comprises determining if condition of the target nerve is worsening or improving.

14. An implantable medical device comprising:
- means for delivering stimulation energy to a target nerve;
- means for acquiring compound action potentials responsive to the delivered stimulation energy; and
- means for assessing a condition of the target nerve based at least in part on the compound action potentials.

* * * * *